(12) United States Patent
Alisi et al.

(10) Patent No.: US 8,871,948 B2
(45) Date of Patent: Oct. 28, 2014

(54) (AZA)INDOLE DERIVATIVE SUBSTITUTED IN POSITION 5, PHARMACEUTICAL COMPOSITION COMPRISING IT, INTERMEDIATE COMPOUNDS AND PREPARATION PROCESS THEREFOR

(71) Applicant: Aziende Chimiche Riunite Angelini Francesco A.C.R.A.F.S.p.A., Rome (IT)

(72) Inventors: Maria Alessandra Alisi, Rome (IT); Guido Furlotti, Rome (IT); Nicola Cazzolla, Albano Laziale (IT); Caterina Maugeri, Rome (IT); Patrizia Dragone, Rome (IT); Barbara Garofalo, Rome (IT); Isabella Coletta, Rome (IT); Giorgina Mangano, Rome (IT); Beatrice Garrone, Rome (IT)

(73) Assignee: Aziende Chimiche Riunite Angelini Francesco A.C.R.A.F. S.p.A., Rome (IT)

( * ) Notice: Subject to any disclaimer, the term of this patent is extended or adjusted under 35 U.S.C. 154(b) by 0 days.

(21) Appl. No.: 13/768,013

(22) Filed: Feb. 15, 2013

(65) Prior Publication Data
US 2013/0158269 A1 Jun. 20, 2013

Related U.S. Application Data

(62) Division of application No. 12/745,356, filed as application No. PCT/EP2008/067622 on Dec. 16, 2008, now Pat. No. 8,399,477.

(30) Foreign Application Priority Data

Dec. 28, 2007 (EP) .................................. 07425830

(51) Int. Cl.
*C07D 209/04* (2006.01)
*C07D 207/44* (2006.01)

(52) U.S. Cl.
USPC ........... 548/469; 548/509; 548/510; 548/511; 548/548

(58) Field of Classification Search
USPC .......................... 548/469, 509, 510, 511, 548
See application file for complete search history.

(56) References Cited

U.S. PATENT DOCUMENTS

| | | | |
|---|---|---|---|
| 4,139,634 A | 2/1979 | Pigerol et al. | |
| 8,017,644 B2 | 9/2011 | Alisi et al. | |
| 2002/0052373 A1* | 5/2002 | Zorn et al. ................... | 514/248 |
| 2003/0225036 A1 | 12/2003 | Kolesnikov et al. | |
| 2007/0027179 A1 | 2/2007 | Wei et al. | |
| 2007/0244159 A1 | 10/2007 | Ruah et al. | |
| 2008/0039460 A1 | 2/2008 | Honold et al. | |

FOREIGN PATENT DOCUMENTS

| | | |
|---|---|---|
| DE | 27 27 047 | 12/1977 |
| WO | 2004 087704 | 10/2004 |
| WO | 2006 066913 | 6/2006 |
| WO | 2007 042816 | 4/2007 |
| WO | 2008/006663 | 1/2008 |

OTHER PUBLICATIONS

Vane, J. R. et al., "Anti-Inflammatory Drugs and Their Mechanism of Action", Inflamm. Res. 47, Supplement 2, pp. 78-87 (1998).
Ayoub, S.S., et al. "Acetaminophen-Induced Hypothermia in Mice is Mediated by a Prostaglandin Endoperoxide Synthase 1 Gene-Derived Protein", PNAS, vol. 101, No. 30, pp. 11165-11169 (Jul. 27, 2004).
Ivanov, A. et al., "Prostaglandin E2-Synthesizing Enzymes in Fever: Differential Transcriptional Regulation", Am. J. Physiol. Regul. Integr. Comp. Physiol. 283, pp. R1104-R1117 (2002).
Kudo, I., et al. "Prostaglandin E Synthase, a Terminal Enzyme for Prostaglandin E2 Biosynthesis", Journal of Biochemistry and Molecular Biology, vol. 38, No. 6, pp. 633-638 (Nov. 2005).
Jakobsson, P.-J., et al., "Identification of Human Prostaglandin E Synthase: A Microsomal, Glutathione-Dependent, Inducible Enzyme, Constituting a Potential Novel Drug Target", Proc. Natl. Acad. Sci. vol. 96, pp. 7220-7225 (Jun. 1999).
Lazarus, M., et al., "Biochemical Characterization of Mouse Microsomal Prostaglandin E Synthase-1 and its Colocalization with Cyclooxygenase-2 in Peritoneal Macrophages", Archives of Biochemistry and Biophysics, vol. 397, No. 2, pp. 336-341 (2002).
Murakami, M., et al., "Regulation of Prostaglandin E2 Biosynthesis by Inducible Membrane-associated Prostaglandin E2 Synthase That Acts in Concert with Cyclooxygenase-2", The Journal of Biological Chemistry, vol. 275, No. 42, pp. 32783-32792 (2000).
Yamagata, K., et al., "Coexpression of Microsomal-Type Prostaglandin E Synthase with Cyclooxygenase-2 in Brain Endothelial Cells of Rats during Endotoxin-Induced Fever", The Journal of Neuroscience, 21(8), pp. 2669-2677 (Apr. 15, 2001).
Stichtenoth, D. O., et al. "Microsomal Prostaglandin E Synthase is Regulated by Proinflammatory Cytokines and Glucocorticoids in Primary Rheumatoid Synovial Cells", The Journal of Immulogy, pp. 469-474 (2001).
Samuelsson, B., et al., "Membrane Prostaglandin E Synthase-1: A Novel Therapeutic Target", Pharmacological Reviews, vol. 59, No. 3, pp. 207-224 (Jul. 16, 2007).

(Continued)

*Primary Examiner* — Niloofar Rahmani
(74) *Attorney, Agent, or Firm* — Oblon, Spivak, McClelland, Maier & Neustadt, L.L.P.

(57) ABSTRACT

An (aza)indole derivative substituted in position 5, of formula (I) in which X, Y, Z, G1, G2, G3, R1, W, and R2 have the meanings given in the description, a pharmaceutical composition comprising it, and also intermediate compounds and a preparation process therefor.

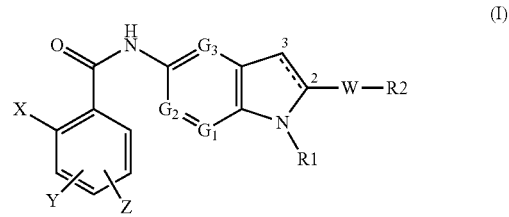

(I)

5 Claims, No Drawings

(56) References Cited

OTHER PUBLICATIONS

Howe, L. R. "Inflammation and Breast Cancer. Cyclooxygenase/Prostaglandin Signaling and Breast Cancer", Breast Cancer Research 9:210, pp. 1-9 (2007).

Castellone, M. D., et al., "Prostaglandin E2 Promotes Colon Cancer Cell Growth Through a G s-Axin-β-Catenin Signaling Axis", Science 310, pp. 1504-1510 (2005).

Mehrotra, S., et al., "Microsomal Prostaglandin E2 Synthase-I in Breast Cancer: A Potential Target for Therapy", Journal of Pathology 208, pp. 356-363 (2006).

Nakano, Y., et al. "Induction of Macrophagic Prostaglandin E2 Synthesis by Glioma Cells", J. Neurosurgery, vol. 104, pp. 574-582 (2006).

Wang, D., et al., "Prostaglandins and Cancer" GUT, vol. 55, pp. 115-122 (2006).

Han, C., et al., "Prostaglandin E2 Receptor EP1 Transactivates EGFR/MET Receptor Tyrosine Kinases and Enhances Invasiveness in Human Hepatocellular Carcinoma Cells", Journal of Cellular Physiology, vol. 207, pp. 261-270 (2006).

Thoren, S. et al., "Coordinate Up- and down-Regulation of Glutathione-dependent Prostaglandin E Synthase and Cyclooxygenase-2 in A549 cells Inhibition by NS-398 and Leukotriene C4", Eur. J. Biochem., vol. 267, pp. 6428-6434 (2000).

Stock, J. L., et al., "The Prostaglandin E2 EP1 Receptor Mediates Pain Perception and Regulates Blood Pressure", The Journal of Clinical Investigation, vol. 107, No. 3, pp. 325-331 (Feb. 2001).

Vippagunta et al., "Crystalline Solids" Advanced Drug Delivery Reviews, vol. 48, pp. 3-26 (2001).

Netterwald, "Screened Gems" Drug Discovery & Development, vol. 9(9), pp. 22-26 (2007).

Lucaites et al., Naunyn-Schmiedeberg's Archives of Pharmacology (2005), 371(3), 178-184.

\* cited by examiner

(AZA)INDOLE DERIVATIVE SUBSTITUTED IN POSITION 5, PHARMACEUTICAL COMPOSITION COMPRISING IT, INTERMEDIATE COMPOUNDS AND PREPARATION PROCESS THEREFOR

CROSS REFERENCES TO RELATED APPLICATIONS

This application is a divisional application of U.S. patent application Ser. No. 12/745,356, filed Jun. 18, 2010, which was 371 of International Patent Application No. PCT/EP2008/067622, filed on Dec. 16, 2008, and claims priority to European Patent Application No. 07425830.2, filed on Dec. 28, 2007.

The present invention relates to an (aza)indole derivative substituted in position 5, to a pharmaceutical composition comprising it, to intermediate compounds and to a preparation process therefor.

More particularly, the present invention relates to an (aza) indole derivative substituted in position 5, which has inhibitory activity on mPGES-1.

It is known that prostaglandins (PG) are oxygenated fatty acids synthesized and released into the extracellular space, and then into the plasma, urine and other biological fluids.

They are important bioregulators, but also inflammation mediators that modulate intracellular reactions and intercellular communication.

The prostaglandins $E_2$ ($PGE_2$) have an important physiological role of regulating renal function, vascular homeostasis, bone remodeling, induction of fever, gastrointestinal function and pregnancy. Besides these physiological functions, the $PGE_2$ prostaglandins behave as potent mediators of acute inflammation (inducing hyperalgesia, vasodilatation and discharge of fluids from vessels: Vane J. R. and Botting R. M. 1997 "Anti-inflammatory drugs and their mechanism of action" Inflamm. Res. 47 (2): p. 78) and chronic inflammation. Specifically, the $PGE_2$ prostaglandins are particularly abundant in articular inflammatory pathologies. $PGE_2$ prostaglandins also play a role in pain and are potent pyretic agents (Ayoub S. S. et al., 2004 "Acetaminophen-induced hypothermia in mice is mediated by a prostaglandin endoperoxide synthase 1 gene-derived protein", PNAS 101: 11165-11169; Ivanov A. et al. 2002 "Prostaglandin $E_2$-synthesizing enzymes in fever: differential transcriptional regulation", Am. J. Physiol. Regul. Integr. Comp. Physiol. 283: R1104-R1117).

The enzyme responsible for the synthesis of $PGE_2$ prostaglandins is prostaglandin E synthase (PGES), which converts the endoperoxide $PGH_2$, formed from arachidonic acid by the action of cyclooxygenases, into $PGE_2$. The activity of PGES has been found both in the cytosolic fraction and membrane-bound in various types of cells.

Three enzymatic forms have been identified (Kudo I. et al. 2005 "Prostaglandin E synthase, a terminal enzyme for prostaglandin $E_2$ biosynthesis", Journal of Biochemistry and Molecular Biology 38, 633-638); among these, microsomal PGES-1 (mPGES-1) is a membrane-bound enzyme that requires glutathione as an essential cofactor for its activity.

The expression of mPGES-1 is induced by pro-inflammatory stimuli such as IL-1β or LPS (Proc. Natl. Acad. Sci. 96: 7220, 1999). It is co-localized together with COX-2 on the endoplasmatic reticulum and on the nuclear envelope (Lazarus M. et al. 2002 "Biochemical characterization of mouse microsomal prostaglandin E synthase-1 and its colocalization with cyclooxygenase-2 in peritoneal macrophages" Arch. Biochem. Biophys. 397: 336; Murakami M. et al. 2000 "Regulation of prostaglandin E2 biosynthesis by inducible membrane-associated prostaglandin E2 synthase that acts in concert with cyclooxygenase-2" J. Biol. Chem. 275: 32783; Yamagata K. et al. 2001 "Coexpression of microsomal-type prostaglandin E synthase with cyclooxygenase-2 in brain endothelial cells of rats during endotoxin-induced fever" J. Neurosci. 15; 21(8): 2669-77). Although the two enzymes (COX-2 and mPGES-1) have a functional connection and co-expression, their rate of induction differs in a few cellular systems, indicating different regulatory induction mechanisms (J. Immunol. 167: 469, 2001).

Drugs that inhibit the enzyme COX-2 have been shown to be effective in alleviating inflammation and pain in chronic inflammatory pathologies such as arthritis, but their prolonged use may induce tissue damage caused by an overproduction of cytokines, for instance TNFα and IL-1β (Stichtenoth D. O. 2001 "Microsomal prostaglandin E synthase is regulated by proinflammatory cytokines and glucocorticoids in primary rheumatoid synovial cells" J. Immunol. 167: 469). In addition, the prolonged use of these drugs is associated with cardiovascular side effects. This has led to the withdrawal from the market of a number of selective COX-2 inhibitors and to a revision of the indications for the entire class of these drugs.

Recent research efforts are directed towards overcoming the side effects of COX-2 inhibitors by studying mPGES-1 inhibitors for the purpose of developing drugs that are active in the treatment of inflammation and pain (B. Samuelsson et al. "Membrane Prostaglandin E Synthase-1: A Novel Therapeutic Target" Pharmacol. Rev. 59:207-224, 2007).

In addition, numerous studies have demonstrated that the $PGE_2$ prostaglandins are tumor-promoting factors (L. R. Howe, "Inflammation and breast cancer. Cyclooxygenase/prostaglandin signaling and breast cancer", Breast cancer research 2007, 9:210, Castellone M. D. et al. 2005 "Prostaglandin $E_2$ promotes colon cancer growth through a novel Gs-Axin-B-catenin", Science 310, 1504-1510; Mehrotra S., et al. 2006 "Microsomal prostaglandin $E_2$ in breast cancer: a potential target for therapy", J. Pathol. 208(3): 356-63; Nakano et al. 2006 "Induction of macrophagic prostaglandin E2 synthesis by glioma cells" J. Neurosurgery 104(4), 574-582) that are involved in angiogenesis, cell proliferation and cell migration functions. Selective FANS and COX-2 inhibitors are also found to inhibit various types of tumors, including colonrectal, oesophageal, breast, lung and bladder tumors by means of inhibiting $PGE_2$. $PGE_2$ prostaglandins derived from COX-2 induce tumor growth by means of binding to the actual receptors and activating signals for controlling cell proliferation, migration, apoptosis and angiogenesis (Wang D. et al. 2006 "Prostaglandin and cancer" Gut. 55 (1):115-22; Han C. et al. 2006 "Prostaglandin $E_2$ receptor EP1 transactivates EGFR/MET receptor tyrosine kinases and enhances invasiveness in human hepatocellular carcinoma cells", Journal of Cellular Physiology 207: 261-270).

An (aza)indole derivative substituted in position 5 that has selective inhibitory activity on mPGES-1 has now been found. The wording "(aza)indole derivative" is intended to represent a compound within formula (I) hereinbelow, wherein the basic nucleus, represented by an indole ring, can have one or more carbon atoms in the 4, 6, and 7 position optionally replaced with a nitrogen atom and a single or double bond between the carbon atoms in the 2- and 3-position.

In a first aspect, the present invention relates to an (aza) indole derivative substituted in position 5, of formula (I):

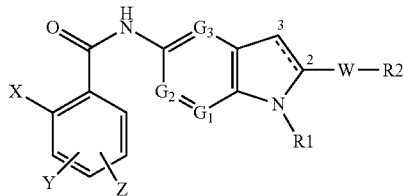

Formula (I)

in which:

X is a halogen atom or a $(C_1-C_3)$alkyl, trifluoromethyl, nitro, amino, cyano, di$(C_1-C_3)$alkylamino, hydroxy, $(C_1-C_3)$ alkoxy, phenyl or $(C_1-C_3)$alkylphenyl group;

Y and Z, which may be identical or different, are a hydrogen or halogen atom, or a $(C_1-C_3)$alkyl, trifluoromethyl, nitro, amino, di$(C_1-C_3)$alkylamino, hydroxy, $(C_1-C_3)$alkoxy, phenyl, COOH, $(C_1-C_3)$alkyl-COOH, $(C_2-C_3)$alkenyl-COOH, COOR, wherein R is a linear or branched $(C_1-C_6)$ alkyl or hydroxyalkyl group, $CONH_2$, $SO_2CH_3$, $SO_2NHCH_3$ or $NHSO_2CH_3$ group;

G1, G2, and G3, which may be identical or different, are a nitrogen atom or a CH group;

R1 is a $(C_1-C_6)$alkyl, $(C_3-C_7)$cycloalkyl, $(C_1-C_6)$alkylOR$^I$, $(CH_2)_nNR^{II}R^{III}$, $(CH_2)_nCONR^{II}R^{III}$, $(CH_2)_nCOR^I$, $(CH_2)_nCOOR^{II}$, $(CH_2)_nOCOR^I$, $SO_2R^I$, $(CH_2)_nNR^{II}SO_2R^I$, $(CH_2)_nSO_2R^I$ group, optionally substituted with 1 to 3 hydroxy groups, wherein n is an integer from 1 to 6, $R^I$ is a $(C_1-C_3)$alkyl, or $(C_1-C_3)$alkylOH group, and $R^{II}$ and $R^{III}$, which may be identical or different, are a hydrogen atom or a $(C_1-C_3)$alkyl group;

W is a σ bond, or a $(C_1-C_6)$alkyl, $(C_2-C_6)$alkenyl, $O(C_1-C_6)$ alkyl, $O(C_2-C_6)$alkenyl, $C(O)NH$, $(CH_2)_pCO(CH_2)_q$, or $(CH_2)_pC(OH)(CH_2)_q$, group, wherein p and q, which may be identical or different, are an integer from 0 to 3;

R2 is a phenyl, pyridine or $(C_3-C_7)$cycloalkyl group, optionally substituted with 1 to 3 substituents, which may be identical or different, represented by a L-M group, wherein L is a σ bond, or a $(C_1-C_6)$alkyl, $(C_2-C_6)$alkenyl, $(C_2-C_6)$ alkinyl, $O(C_1-C_6)$alkyl, $O(C_2-C_6)$alkenyl, $O(C_2-C_6)$alkinyl group, and M is a hydrogen or halogen atom, or a OH, $CF_3$, $NO_2$, CN, $COOR^{II}$, $SO_2NHR^{II}$, $CH_2CONR^{II}R^{III}$, $NR^{II}R^{III}$, $SO_2R^{IV}$, $NHSO_2R^{IV}$, $POR^{IV}R^V$, or $OPOR^{IV}R^V$ group, wherein $R^{II}$ and $R^{III}$, which may be identical or different, have the meaning above, and $R^{IV}$ and $R^V$, which may be identical or different, are a $(C_1-C_3)$alkyl group; provided that when G1, G2, and G3 are all a CH group, R1 is a $(C_1-C_6)$alkyl or $(C_3-C_7)$cycloalkyl group, optionally substituted with 1 to 3 hydroxy groups, W is a σ bond, and the bond between the carbon atoms in the 2 and 3 position is a double bond, R2 is not a phenyl or pyridine group, optionally substituted with 1 to 3 substituents, which may be identical or different, selected from halogen, $(C_1-C_6)$alkyl optionally substituted with a hydroxy group, trifluoromethyl, nitro, amino, di$(C_1-C_3)$alkylamino, hydroxy, $(C_1-C_3)$alkoxy, COOH, $COOR^{II}$, $SO_2CH_3$, $SO_2NHCH_3$, $NHSO_2CH_3$, $POR^{IV}R^V$, $OPOR^{IV}R^V$, $(C_1-C_6)$alkyl-COOH, and $(C_2-C_6)$alkenyl-COOH;

and provided that when G1 is N, and G2 and G3 are a CH group, R2 is not a divalent aromatic group substituted with one L-M group represented by $O(C_1-C_6)$alkyl, $O(C_2-C_6)$alkenyl, and $O(C_2-C_6)$ alkinyl group;

and the physiologically acceptable addition salts, stereoisomers, enantiomers, hydrates, solvates and polymorphic forms thereof.

The dotted line between the carbon atoms in the 2 and 3 position means that such a bond can be a single or a double bond. The chain of the various alkyl groups that may be present in the compound of formula (I) may be linear or branched.

In the case of certain substituents, the compound of formula (I) according to the present invention may contain an asymmetric carbon atom and may thus be in the form of stereoisomers and enantiomers. Typical examples of such substituents are 2-butanol, 2-methylbutyl, 2-butenoic acid, 2-methylpropanoic acid and 1,2-pentane diol.

Preferably, the halogen is bromine, chlorine or fluorine.

Preferred meanings of X are halogen, $(C_1-C_3)$alkyl, trifluoromethyl, nitro, cyano and $(C_1-C_3)$alkoxy. Particularly preferred meanings of X are Cl, Br, F, trifluoromethyl and nitro.

Preferred meanings of Y and Z are H, halogen, nitro, COOH, $(C_1-C_3)$alkyl, trifluoromethyl and $(C_1-C_3)$alkoxy. Particularly preferred meanings of Y and Z are H, Cl, Br, F, trifluoromethyl, nitro, COOH, methyl, ethyl, methoxy and ethoxy.

Preferred meanings of R1 are a $(C_1-C_3)$alkyl, $(C_1-C_3)$alkyl OR$^I$, $(CH_2)_nNR^{II}R^{III}$, $(CH_2)_nCONR^{II}R^{III}$, $(CH_2)_nCOR^I$, $(CH_2)_nCOOR^{II}$, $(CH_2)_nOCOR^I$, $SO_2R^I$, $(CH_2)_nNR^{II}SO_2R^I$, $(CH_2)_nSO_2R^I$ group, optionally substituted with 1 to 3 hydroxy groups, wherein n is an integer from 1 to 4, $R^I$ is a $(C_1-C_3)$alkyl or $(C_1-C_3)$alkylOH group, and $R^{II}$ and $R^{III}$, which may be identical or different, are a hydrogen atom or a $(C_1-C_3)$alkyl group.

Particularly preferred meanings of R1 are a $(C_1-C_3)$alkyl, $(C_1-C_3)$alkylOR$^I$, $(CH_2)_nCONR^{II}R^{III}$, $(CH_2)_nCOR^I$, $(CH_2)_n$ $COOR^{II}$, $(CH_2)_nOCOR^I$, $SO_2R'$, $(CH_2)_nNR^{II}SO_2R^I$, $(CH_2)_n$ $SO_2R^I$ group, optionally substituted with 1 to 3 hydroxy groups, wherein n is an integer from 1 to 3, $R^I$ is a $CH_3$, $C_2H_5$, $CH_2OH$, or $C_2H_4OH$ group, and $R^{II}$ and $R^{III}$, which may be identical or different, are a hydrogen atom or a $CH_3$, $C_2H_5$ group.

Preferred meanings of W are a σ bond, or a $(C_1-C_3)$alkyl, $(C_2-C_4)$alkenyl, $O(C_1-C_3)$alkyl, $O(C_2-C_3)$alkenyl, C(O)NH, $(CH_2)_pCO(CH_2)_q$, or $(CH_2)_pC(OH)(CH_2)_q$ group, wherein p and q, which may be identical or different, are an integer from 1 to 3.

Particularly preferred meanings of W are a σ bond, or a $CH_2$, $C_2H_4$, CH=CH, $OCH_2$, $OC_2H_4$, OCH=CH, C(O)NH, $(CH_2)_pCO(CH_2)_q$, or $(CH_2)_pC(OH)(CH_2)_q$ group, wherein p and q, which may be identical or different, are an integer from 1 to 2.

Preferred meanings of R2 are a phenyl, pyridine or $(C_3-C_7)$ cycloalkyl group, optionally substituted with 1 to 2 substituents, which may be identical or different, represented by a L-M group, wherein L is a a bond, or a $(C_1-C_3)$alkyl, $(C_2-C_4)$ alkenyl, $(C_2-C_4)$alkinyl, $O(C_1-C_3)$alkyl, $O(C_2-C_4)$alkenyl, $O(C_2-C_4)$alkinyl group, and M is a hydrogen or halogen atom, or a $CF_3$, CN, $COOR^{II}$, $SO_2NHR^{II}$, $CH_2CONR^{II}R^{III}$, $NR^{II}$ $R^{III}$, $SO_2R^{IV}$, $NHSO_2R^{IV}$, $POR^{IV}R^V$, or $OPOR^{IV}R^V$ group, wherein $R^{II}$ and $R^{III}$, which may be identical or different, are a hydrogen atom or a $(C_1-C_3)$alkyl group, and $R^{IV}$ and $R^V$, which may be identical or different, are a $(C_1-C_3)$alkyl group.

Particularly preferred meanings of R2 is a phenyl, pyridine or $(C_3-C_7)$cycloalkyl group, optionally substituted with 1 substituent represented by a G-M group, wherein L is a G bond, or a $CH_2$, $C_2H_4$, CH=CH, C≡C, $OCH_2$, $OC_2H_4$, OCH=CH, OC≡C group, and M is a hydrogen or halogen atom, or a $CF_3$, CN, $COOR^{II}$, $SO_2NHR^{II}$, $CH_2CONR^{II}R^{III}$, NR$^{II}$R$^{III}$, SO$_2$R$^{IV}$, NHSO$_2$R$^{IV}$, POR$^{IV}$R$^{V}$, or OPOR$^{IV}$R$^{V}$ group, wherein R$^{II}$ and R$^{III}$, which may be identical or different, are a hydrogen atom or a CH$_3$, C$_2$H$_5$ group, and R$^{IV}$ and R$^{V}$, which may be identical or different, are a CH$_3$ or C$_2$H$_5$ group.

A first particularly preferred meaning of the group W—R2 is where W is a σ bond, or a CH$_2$ or C$_2$H$_4$ group and R2 is a phenyl group optionally substituted with 1 to 3 substituents, which may be identical or different, selected from Br, Cl, and F atom, and CH$_3$, C$_2$H$_5$, OCH$_3$, OC$_2$H$_5$, CN, CH$_2$CN, and CH$_2$CONH$_2$ group.

A second particularly preferred meaning of the group W—R2 is where W is a σ bond, or a CH$_2$ or C$_2$H$_4$ group and R2 is a pyridine group optionally substituted with 1 to 3 substituents, which may be identical or different, selected from Br, Cl, and F atom, and CH$_3$, C$_2$H$_5$, OCH$_3$, OC$_2$H$_5$, CN, CH$_2$CN, and CH$_2$CONH$_2$ group.

A third particularly preferred meaning of the group W—R2 is where W is a σ bond, or a CH$_2$ or C$_2$H$_4$ group and R2 is a cyclohexyl group optionally substituted with 1 to 3 substituents, which may be identical or different, selected from Br, Cl, and F atom, and CH$_3$, C$_2$H$_5$, OCH$_3$, OC$_2$H$_5$, CN, CH$_2$CN, and CH$_2$CONH$_2$ group.

Depending on the nature of the substituents, the compound of formula (I) may form addition salts with physiologically acceptable organic or mineral acids or bases.

Typical examples of physiologically acceptable mineral acids are hydrochloric acid, hydrobromic acid, sulfuric acid, phosphoric acid and nitric acid.

Typical examples of suitable physiologically acceptable organic acids are acetic acid, ascorbic acid, benzoic acid, citric acid, fumaric acid, lactic acid, maleic acid, methanesulfonic acid, oxalic acid, para-toluenesulfonic acid, benzensulfonic acid, succinic acid, tannic acid and tartaric acid.

Typical examples of suitable physiologically acceptable mineral bases are: ammonia, calcium, magnesium, sodium and potassium.

Typical examples of suitable physiologically acceptable organic bases are: arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, N-methylglucamine, glucamine, glucosamine, histidine, N-(2-hydroxyethyl)piperidine, N-(2-hydroxyethyl)pyrrolidine, isopropylamine, lysine, methylglucamine, morpholine, piperazine, piperidine, theobromine, triethylamine, trimethylamine, tripropylamine and tromethamine.

In a second aspect, the present invention relates to a process for preparing an (aza)indole derivative substituted in position 5, of formula (I):

Formula (I)

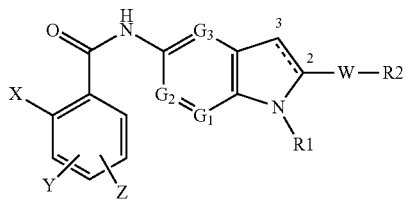

in which X, Y, Z, G1, G2, G3, W, R1 and R2 have the meanings given above,
and the physiologically acceptable addition salts, stereoisomers, enantiomers, hydrates, sulfates and polymorphic forms thereof, a) by reacting a compound of formula (II):

(II)

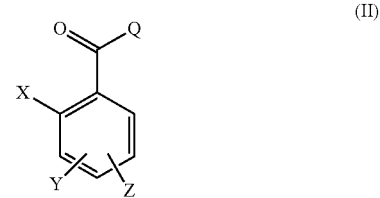

in which
X, Y and Z have the meanings given above, and
Q is a halogen atom or a hydroxy group,
with a compound of formula (III):

(III)

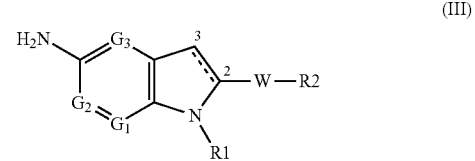

in which
G1, G2, G3, R1, R2 and W have the meanings given above, to give a compound of formula (I):

Formula (I)

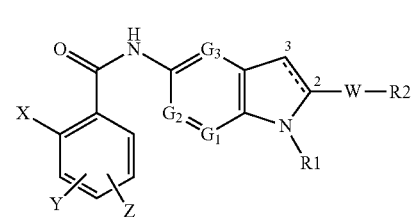

in which
X, Y, Z, G1, G2, G3, R1, R2 and W have the meanings given above, and
b) forming, if so desired, a physiologically acceptable addition salt of the compound of formula (I) from step (a).

According to a first embodiment, the abovementioned step (a) is performed by reacting a compound of formula (II) in which Q is Cl with an amine of formula (III) in the presence of a suitable acid acceptor according to standard techniques.

According to a second embodiment, the abovementioned step (a) is performed by reacting a compound of formula (II) in which Q is OH with an amine of formula (III) in the presence of a suitable coupling agent according to standard techniques.

Further, the reaction of step (a) can also be conducted in solid phase by preliminary linking the compound of formula (III) to a preparative resin, such as, for example PL-FMP Resin, manufactured by from Polymer Laboratories. In this case, a cleavage step, in which the resulting compound of formula (I) is removed from the resin is made after step (a). Such a cleavage step is made with conventional techniques, such as, for example, treatment with trifluoroacetic acid.

When the compound of formula (I) is intended to have a single bond between the carbon atoms in the 2- and 3-position, a reduction step is made after step (a). Such a reduction step is made with conventional techniques, such as, for example, treatment with tin in the presence of a strong acid.

When R1 is represented by a $(CH_2)_nCOOR^{II}$ group, and $R^{II}$ is an alkyl group, the corresponding acid, wherein $R^{II}$ is a hydrogen atom, may be obtained by hydrolysis, according to standard techniques, such as, for example, in the presence of a strong base like NaOH.

The intermediate compounds of formula (III) are novel.

According to a third aspect, the present invention also relates to a compound of formula (III):

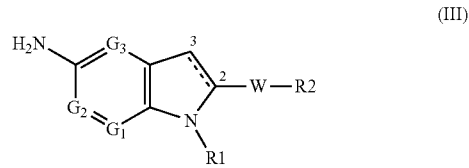

(III)

wherein
G1, G2, and G3, which may be identical or different, are a nitrogen atom or a CH group;
R1 is a $(C_1$-$C_6)$alkyl, $(C_3$-$C_7)$cycloalkyl, $(C_1$-$C_6)$alkyl$OR^I$, $(CH_2)_nCONR^{II}R^{III}$, $(CH_2)_nCOR^I$, $(CH_2)_nCOOR^{II}$, $(CH_2)_nOCOR^I$, $SO_2R^I$, $(CH_2)_nNR^{II}SO_2R^I$, $(CH_2)_nSO_2R^I$ group, optionally substituted with 1 to 3 hydroxy groups, wherein n is an integer from 1 to 6, $R^I$ is a $(C_1$-$C_3)$alkyl, or $(C_1$-$C_3)$alkylOH group, and $R^{II}$ and $R^{III}$, which may be identical or different, are a hydrogen atom or a $(C_1$-$C_3)$alkyl group;
W is a σ bond, or a $(C_1$-$C_6)$alkyl, $(C_2$-$C_6)$alkenyl, $O(C_1$-$C_6)$alkyl, $O(C_2$-$C_6)$alkenyl, C(O)NH, $(CH_2)_pCO(CH_2)_q$, or $(CH_2)_pC(OH)(CH_2)_q$, group, wherein p and q, which may be identical or different, are an integer from 0 to 3; and
R2 is a phenyl, pyridine or $(C_4$-$C_7)$cycloalkyl group, optionally substituted with 1 to 3 substituents, which may be identical or different, represented by a L-M group, wherein L is a σ bond, or a $(C_1$-$C_6)$alkyl, $(C_2$-$C_6)$alkenyl, $(C_2$-$C_6)$alkinyl, $O(C_1$-$C_6)$alkyl, $O(C_2$-$C_6)$alkenyl, $O(C_2$-$C_6)$alkinyl group, and M is a hydrogen or halogen atom, or a OH, $CF_3$, $NO_2$, CN, $COOR^{II}$, $SO_2NHR^{II}$, $CH_2CONR^{II}R^{III}$, $NR^{II}R^{III}$, $SO_2R^{IV}$, $NHSO_2R^{IV}$, $POR^{IV}R^V$, or $OPOR^{IV}R^V$ group, wherein $R^{II}$ and $R^{III}$, which may be identical or different, have the meaning above, and $R^{IV}$ and $R^V$, which may be identical or different, are a $(C_1$-$C_3)$alkyl group,
provided that
when G1, G2, and G3 are all a CH group, R1 is a $(C_1$-$C_6)$alkyl or $(C_3$-$C_7)$cycloalkyl group, optionally substituted with 1 to 3 hydroxy groups, W is a σ bond, and the bond between the carbon atoms in the 2 and 3 position is a double bond, R2 is not a phenyl or pyridine group, optionally substituted with 1 to 3 substituents, which may be identical or different, selected from halogen, $(C_1$-$C_6)$alkyl optionally substituted with a hydroxy group, trifluoromethyl, nitro, amino, di$(C_1$-$C_3)$alkylamino, hydroxy, $(C_1$-$C_3)$alkoxy, COOH, $COOR^{II}$, $SO_2CH_3$, $SO_2NHCH_3$, $NHSO_2CH_3$, $POR^{IV}R^V$, $(C_1$-$C_6)$alkyl-COOH, and $(C_2$-$C_6)$alkenyl-COOH
and provided that
when G1 is N, and G2 and G3 are a CH group, R2 is not a divalent aromatic group substituted with one L-M group represented by $O(C_1$-$C_6)$alkyl, $O(C_2$-$C_6)$alkenyl, and $O(C_2$-$C_6)$alkinyl group.

Preferred meanings of R1 is a $(C_1$-$C_3)$alkyl, $(C_1$-$C_3)$alkyl$OR^I$, $(CH_2)_nCONR^{II}R^{III}$, $(CH_2)_nCOR^I$, $(CH_2)_nCOOR^{II}$, $(CH_2)_nOCOR^I$, $SO_2R^I$, $(CH_2)_nNR^{II}SO_2R^I$, $(CH_2)_nSO_2R^I$ group, optionally substituted with 1 to 3 hydroxy groups, wherein n is an integer from 1 to 4, $R^I$ is a $(C_1$-$C_3)$alkyl or $(C_1$-$C_3)$alkylOH group, and $R^{II}$ and $R^{III}$, which may be identical or different, are a hydrogen atom or a $(C_1$-$C_3)$alkyl group.

Particularly preferred meanings of R1 is a $(C_1$-$C_3)$alkyl, $(C_1$-$C_3)$alkyl$OR^I$, $(CH_2)_nCONR^{II}R^{III}$, $(CH_2)_nCOR^I$, $(CH_2)_nCOOR^{II}$, $(CH_2)_nOCOR^I$, $SO_2R^I$, $(CH_2)_nNR^{II}SO_2R^I$, $(CH_2)_nSO_2R^I$ group, optionally substituted with 1 to 3 hydroxy groups, wherein n is an integer from 1 to 3, $R^I$ is a $CH_3$, $C_2H_5$, $CH_2OH$, or $C_2H_4OH$ group, and $R^{II}$ and $R^{III}$, which may be identical or different, are a hydrogen atom or a $CH_3$, $C_2H_5$ group.

Preferred meanings of W are a bond, or a $(C_1$-$C_3)$alkyl, $(C_2$-$C_4)$alkenyl, $O(C_1$-$C_3)$alkyl, $O(C_2$-$C_3)$alkenyl, C(O)NH, $(CH_2)_pCO(CH_2)_q$, or $(CH_2)_pC(OH)(CH_2)_q$ group, wherein p and q, which may be identical or different, are an integer from 1 to 3.

Particularly preferred meanings of W are a bond, or a $CH_2$, $C_2H_4$, CH=CH, $OCH_2$, $OC_2H_4$, OCH=CH, C(O)NH, $(CH_2)_pCO(CH_2)_q$, or $(CH_2)_pC(OH)(CH_2)_q$ group, wherein p and q, which may be identical or different, are an integer from 1 to 2.

Preferred meanings of R2 is a phenyl, pyridine or $(C_4$-$C_7)$cycloalkyl group, optionally substituted with 1 to 2 substituents, which may be identical or different, represented by a L-M group, wherein L is a a bond, or a $(C_1$-$C_3)$alkyl, $(C_2$-$C_4)$alkenyl, $(C_2$-$C_4)$alkinyl, $O(C_1$-$C_3)$alkyl, $O(C_2$-$C_4)$alkenyl, $O(C_2$-$C_4)$alkinyl group, and M is a hydrogen or halogen atom, or a $CF_3$, CN, $COOR^{II}$, $SO_2NHR^{II}$, $CH_2CONR^{II}R^{III}$, $NR^{II}R^{III}$, $SO_2R^{IV}$, $NHSO_2R^{IV}$, $POR^{IV}R^V$, or $OPOR^{IV}R^V$ group, wherein $R^{II}$ and $R^{III}$, which may be identical or different, are a hydrogen atom or a $(C_1$-$C_3)$alkyl group, and $R^{IV}$ and $R^V$, which may be identical or different, are a $(C_1$-$C_3)$alkyl group.

Particularly preferred meanings of R2 is a phenyl, pyridine or $(C_4$-$C_7)$cycloalkyl group, optionally substituted with 1 substituent represented by a L-M group, wherein L is a σ bond, or a $CH_2$, $C_2H_4$, CH=CH, C≡C, $OCH_2$, $OC_2H_4$, OCH=CH, OC≡C group, and M is a hydrogen or halogen atom, or a $CF_3$, CN, $COOR^{II}$, $SO_2NHR^{II}$, $CH_2CONR^{II}R^{III}$, $NR^{II}R^{III}$, $SO_2R^{IV}$, $NHSO_2R^{IV}$, $POR^{IV}R^V$, or $OPOR^{IV}R^V$ group, wherein $R^{II}$ and $R^{III}$, which may be identical or different, are a hydrogen atom or a $CH_3$, $C_2H_5$ group, and $R^{IV}$ and $R^V$, which may be identical or different, are a $CH_3$ or $C_2H_5$ group.

A first particularly preferred meaning of the group W—R2 is where W is a σ bond, or a $CH_2$ or $C_2H_4$ group and R2 is a phenyl group optionally substituted with 1 to 3 substituents, which may be identical or different, selected from Br, Cl, and F atom, $CH_3$, $C_2H_5$, $OCH_3$, $OC_2H_5$, CN, $CH_2CN$, and $CH_2CONH_2$ group.

A second particularly preferred meaning of the group W—R2 is where W is a σ bond, or a $CH_2$ or $C_2H_4$ group and R2 is a pyridine group optionally substituted with 1 to 3 substituents, which may be identical or different, selected from Br, Cl, and F atom, $CH_3$, $C_2H_5$, $OCH_3$, $OC_2H_5$, CN, $CH_2CN$, and $CH_2CONH_2$ group.

A third particularly preferred meaning of the group W—R2 is where W is a σ bond, or a $CH_2$ or $C_2H_4$ group and R2 is a cyclohexyl group optionally substituted with 1 to 3 substituents, which may be identical or different, selected from Br, Cl, and F atom, $CH_3$, $C_2H_5$, $OCH_3$, $OC_2H_5$, CN, $CH_2CN$, and $CH_2CONH_2$ group.

The investigations on the biological properties of the compound of formula (I) according to the present invention demonstrated that it has an unexpected selective property of inhibiting mPGES-1 and pronounced anti-nociceptive activity in inflammatory pain.

In a fourth aspect, the present invention thus relates to a pharmaceutical composition containing an effective amount of a compound of formula (I), or of a physiologically acceptable addition salt, stereoisomer, enantiomer, hydrate, solvate or polymorphic form thereof, and at least one pharmaceutically acceptable inert ingredient.

In the present description and in the claims, the term "effective amount" refers to an amount that gives an appreciable improvement in at least one symptom or parameter of a specific disorder.

The pharmaceutical composition according to the present invention will be used in the treatment or prevention of disorders associated with the production of prostaglandin $E_2$ ($PGE_2$), for instance inflammatory processes, pain, tumors, neurodegenerative disorders and atherosclerosis.

Advantageously, the pharmaceutical composition according to the present invention will be used in the treatment of pain in chronic inflammatory pathologies such as arthritis, or of tumors, particularly colorectal, oesophageal, breast, lung and bladder tumors.

Preferably, the pharmaceutical compositions of the present invention are prepared in suitable dosage forms comprising an effective dose of at least one compound of formula (I) or of a physiologically acceptable addition salt, stereoisomer, enantiomer, hydrate, solvate or polymorphic form thereof, and at least one pharmaceutically acceptable inert ingredient.

Examples of suitable dosage forms are tablets, capsules, coated tablets, granules, solutions and syrups for oral administration; creams, ointments and antiseptic plasters for topical administration; suppositories for rectal administration and sterile solutions for administration by injection or aerosol or ophthalmic administration.

The dosage forms may also contain other conventional ingredients, for instance: preserving agents, stabilizers, surfactants, buffers, salts for regulating the osmotic pressure, emulsifiers, sweeteners, colorants, flavorings and the like.

If required for particular therapies, the pharmaceutical composition of the present invention may contain other pharmacologically active ingredients whose simultaneous administration is beneficial.

The amount of compound of formula (I) or of a physiologically acceptable addition salt, stereoisomer, enantiomer, hydrate, solvate or polymorphic form thereof, and at least one pharmaceutically acceptable inert ingredient in the pharmaceutical composition of the present invention may vary within a wide range depending on known factors, for instance the type of disease to be treated, the severity of the disease, the body weight of the patient, the dosage form, the chosen route of administration, the number of daily administrations and the efficacy of the chosen compound of formula (I). However, the optimum amount may be easily and routinely determined by a person skilled in the art.

Typically, the amount of compound of formula (I) or of a physiologically acceptable addition salt, stereoisomer, enantiomer, hydrate, solvate or polymorphic form thereof, and at least one pharmaceutically acceptable inert ingredient in the pharmaceutical composition of the present invention will be such that it provides a level of administration of between 0.0001 and 100 mg/kg/day and even more preferably between 0.01 and 10 mg/kg/day.

Clearly, the pharmaceutical formations of the present invention do not necessarily need to contain the entire amount of the compound of formula (I) since the said effective amount may be added by means of administration of a plurality of doses of the pharmaceutical composition of the present invention.

The dosage forms of the pharmaceutical composition of the present invention may be prepared according to techniques that are well known to pharmaceutical chemists, including mixing, granulation, compression, dissolution, sterilization and the like.

The examples that follow serve to further illustrate the invention without, however, limiting it.

EXAMPLE 1

Preparation of Intermediate Compounds a) 1-ethyl-2-(4-methylphenyl)-1H-pyrrolo[2,3-b]pyridin-5-amine To a solution of 2-amino-3-bromo-5-nitropyridine (1.2 g, 5.5 mmol) in anhydrous THF (23 ml), $PdCl_2$ (52 mg, 0.29 mmol), 1,1'-Bis(di-tert-butyl phosphino)ferrocene (D-tBPF, 0.17 g, 0.39 mmol), diisopropylamine (0.81 g, 8.0 mmol), and CuI (22 mg, 0.11 mmol) were added while stirring. To this mixture 4-ethynyltoluene (1.0 ml, 7.9 mmol) was added dropwise over 2.25 hours. The mixture thus obtained was filtered under vacuum through Celite, the residue washed several times with EtOAc.

After evaporation of the solvent, the residue was purified by column chromatography on silica gel ($Et_2$O/n-hexane, $Et_2$O 30%→60%) to give 5-nitro-3-(phenylethynyl)pyridin-2-amine as yellow solid:

$^1$H-NMR ($CDCl_3$): 8.93 (d, J=2.7 Hz, 1H); 8.36 (d, J=2.7 Hz, 1H); 7.42 (AA' of AA'BB' system, 2H); 7.19 (BB' of AA'BB' system, 2H); 5.85 (bs, 2H); 2.39 (s, 3H).

To a suspension of potassium ter-butoxide (0.41 g, 3.7 mmol) in anhydrous DMF (5 ml) a solution of 5-nitro-3-(phenylethynyl)pyridin-2-amine (0.70 g, 2.8 mmol), in DMF (25 ml) was added dropwise while stirring at room temperature. After 1.5 days, iodoethane (0.38 ml, 4.7 mmol) was added and the whole stirred for additional 1.5 days. To the reaction $H_2O$ (50 ml) and EtOAc (100 ml) were then added. The mixture was poured into a separatory funnel, the organic layer separated, the aqueous one thoroughly extracted with EtOAc (50 ml) and combined organic layers washed with brine (2×100 ml). The organic solvent was removed by evaporation under reduced pressure and the residue was purified by column chromatography on silica gel ($Et_2$O/n-hexane, $Et_2$O 10%→20%) to give 1-ethyl-2-(4-methylphenyl)-5-nitro-1H-pyrrolo[2,3-b]pyridine:

$^1$H-NMR ($CDCl_3$): 9.21 (d, J=2.7 Hz, 1H); 8.71 (d, J=2.7 Hz, 1H); 7.40 (AA' of AA'BB' system, 2H); 7.32 (BB' of AA'BB' system, 2H); 6.60 (s, 1H); 4.41 (q, J=7.2 Hz, 2H); 2.45 (s, 3H); 1.31 (t, J=7.2 Hz, 3H)

A solution of 1-ethyl-2-(4-methylphenyl)-5-nitro-1H-pyrrolo[2,3-b]pyridine (0.36 g, 1.3 mmol) in a EtOAc/EtOH (absolute)=4:7 mixture (110 ml) was hydrogenated in $H_2$ atmosphere with the presence of 10% Pd(C) (110 mg) for 2 h. The residue was filtered under vacuum through Celite to remove the catalyst and the solvent evaporated to give crude 1-ethyl-2-(4-methylphenyl)-1H-pyrrolo[2,3-b]pyridin-5-amine which was used without any further purification:

$^1$H-NMR ($CDCl_3$): 7.91 (d, J=3.0 Hz, 1H); 7.39 (AA' of AA'BB' system, 2H); 7.32-7.18 (m, 3H); 6.25 (s, 1H); 4.30 (q, J=7.5 Hz, 2H); 3.32 (bs, 2H); 2.41 (s, 3H); 1.27 (t, J=7.5 Hz, 3H).

b) 1-isopropyl-2-(4-methylphenyl)-1H-pyrrolo[2,3-b]pyridin-5-amine

The process described above in Example 1a) was used, except that isopropylbromide was used instead of iodoethane.

1-isopropyl-2-(4-methylphenyl)-5-nitro-1H-pyrrolo[2,3-b]pyridine:
$^1$H-NMR (CDCl$_3$): 9.18 (d, J=2.4 Hz, 1H); 8.67 (d, J=2.4 Hz, 1H); 7.34 (AA'BB' system, 4H); 6.52 (s, 1H); 4.70 (ept., J=6.9 Hz, 1H); 2.45 (s, 3H); 1.70 (d, J=6.9 Hz, 6H)

1-isopropyl-2-(4-methylphenyl)-1H-pyrrolo[2,3-b]pyridin-5-amine:
$^1$H-NMR (CDCl$_3$): 7.85 (d, J=1.4 Hz, 1H); 7.27 (AA' of AA'BB' system, 2H); 7.16-7.05 (m, 3H); 6.11 (s, 1H); 4.56 (ept., J=7.0 Hz, 1H); 3.85 (bs, 2H); 2.33 (s, 3H), 1.59 (d, J=7.0 Hz, 6H).

c) 1-(2-methoxyethyl)-2-(4-methyl phenyl)-1H-pyrrolo[2,3-b]pyridin-5-amine

The process described above in Example 1a) was used, except that 2-methoxyethylbromide was used instead of iodoethane. 1-(2-methoxyethyl)-2-(4-methylphenyl)-5-nitro-1H-pyrrolo[2,3-]pyridine:
$^1$H-NMR (CDCl$_3$): 9.21 (d, J=2.4 Hz, 1H); 8.71 (d, J=2.4 Hz, 1H); 7.49 (AA' of AA'BB' system, 2H); 7.32 (BB' of AA'BB' system, 2H); 6.62 (s, 1H); 4.54 (t, J=5.6 Hz, 2H); 3.70 (t, J=5.6 Hz, 2H); 3.19 (s, 3H); 2.45 (s, 3H).

1-(2-methoxyethyl)-2-(4-methylphenyl)-1H-pyrrolo[2,3-b]pyridin-5-amine:
$^1$H-NMR (CDCl$_3$): 7.89 (d, J=2.7 Hz, 1H); 7.46 (AA' of AA'BB' system, 2H); 7.25 (BB' of AA'BB' system, 2H); 7.19 (d, J=2.4 Hz, 1H); 6.27 (s, 1H); 4.42 (t, J=6.0 Hz, 2H); 3.68 (t, J=6.0 Hz, 2H); 3.40 (bs, 1H); 3.17 (s, 3H); 2.40 (s, 3H).

d) 1-ethyl-2-(4-fluorophenyl)-1H-pyrrolo[2,3-b]pyridin-5-amine

The process described above in Example 1a) was used, except that 1-ethynyl-4-fluorobenzene was used instead of 4-ethynyltoluene.

3-[(4-fluorophenyl)ethynyl]-5-nitropyridin-2-amine:
$^1$H-NMR (CDCl$_3$/CD$_3$OD): 8.78 (d, J=2.3 Hz, 1H); 8.24 (d, J=2.3 Hz, 1H); 7.43 (m, 2H); 6.97 (m, 2H), 2.05 (s, 3H).

1-ethyl-2-(4-fluorophenyl)-5-nitro-1H-pyrrolo[2,3-b]pyridine
$^1$H-NMR (CDCl$_3$): 9.30 (d, J=2.5 Hz, 1H); 8.80 (d, J=2.5 Hz, 1H); 7.60 (m, 2H); 7.30 (m, 2H); 6.70 (s, 1H); 4.48 (q, J=7.6 Hz, 2H); 1.39 (t, J=7.6 Hz 3H)

1-ethyl-2-(4-fluorophenyl)-1H-pyrrolo[2,3-b]pyridin-5-amine
$^1$H-NMR (CDCl$_3$): 7.90 (d, J=2.4 Hz, 1H); 7.42 (m, 2H); 7.25-7.05 (m, 3H), 6.21 (s, 1H); 4.24 (q, J=7.2 Hz, 2H); 3.50 (bs, 2H); 1.22 (t, J=7.2 Hz, 3H)

e) 2-(4-fluorophenyl)-1-(2-methoxyethyl)-1H-pyrrolo[2,3-b]pyridin-5-amine

The process described above in Example 1a) was used, except that 1-ethynyl-4-fluorobenzene and 2-methoxyethylbromide were used instead of 4-ethynyltoluene and iodoethane, respectively.

2-(4-fluorophenyl)-1-(2-methoxyethyl)-5-nitro-1H-pyrrolo[2,3-b]pyridine:
$^1$H-NMR (CDCl$_3$): 9.23 (d, J=2.6 Hz, 1H); 8.74 (d, J=2.6 Hz, 1H); 7.90-7.20 (2m, 5H); 6.64 (s, 1H); 4.51 (t, J=5.6 Hz, 2H); 3.75 (t, J=5.6 Hz, 2H); 3.20 (s, 3H);

2-(4-fluorophenyl)-1-(2-methoxyethyl)-1H-pyrrolo[2,3-b]pyridin-5-amine:
$^1$H-NMR (CDCl$_3$): 8.00 (d, J=2.2 Hz, 1H); 7.63 (m, 2H); 7.40-7.10 (m, 3H), 6.34 (s, 1H); 4.47 (t, J=5.8 Hz, 2H); 3.80 (t, J=5.8 Hz, 4H); 3.25 (s, 3H).

f) ethyl 4-(5-amino-2-phenyl-1H-indol-1-yl)butanoate

To a solution of 2-phenyl-5-nitroindole (prepared as described in J. Org. Chem. (1966), 31(1), 65-9) (1.5 g; 6.3 mmol) in CH$_3$CN (50 ml) was added K$_2$CO$_3$ (1.7 g; 12.6 mmol). To the mixture thus obtained was then added dropwise ethyl 4-bromobutanoate (3.3 g; 16 mmol) and the resulting mixture was heated to 120° C. under stirring for 18 hours. After cooling, the mixture was poured into water (500 ml) and the crude product was filtered, dried under vacuum to give ethyl 4-(5-nitro-2-phenyl-1H-indol-1-yl)butanoate which was used in the following reaction without any further purification.

$^1$H-NMR (DMSO-d$_6$) 1.08 (t, J=7.16 Hz, 3H); 1.80 (quin, J=7.23 Hz, 2H); 2.15 (t, J=7.00 Hz, 2H); 3.91 (q, J=7.02 Hz, 2H); 4.34 (t, J=7.31 Hz, 2H); 6.84 (s, 1H); 7.47-7.62 (m, 5H); 7.80 (d, J=9.06 Hz, 1H); 8.08 (dd, J=9.21, 2.19 Hz, 1H); 8.59 (d, J=2.34 Hz, 1H).

To a suspension of 10% Pd/C (67 mg, 0.06 mmol) in 95% ethanol (50 ml) a solution of 4-(5-nitro-2-phenyl-1H-indol-1-yl)butanoate (2.2 g; 6 mmol) in 95 ethanol (100 ml) was added (0.1 g; 0.1 mmol) and the mixture underwent hydrogenation in a Parr hydrogenator (H$_2$, 30 psi) for 4 hours.

The residue was filtered under vacuum through Celite to remove the catalyst and the solvent evaporated to give crude ethyl 4-(5-amino-2-phenyl-1H-indol-1-yl)butanoate which was used without any further purification.

$^1$H NMR (DMSO-d$_6$) 1.09 (t, J=7.16 Hz, 3H); 1.78 (quin, J=7.16 Hz, 2H); 2.09 (t, J=7.16 Hz, 2H); 3.92 (q, J=7.21 Hz, 2H); 4.20 (t, J=7.31 Hz, 2H); 6.44 (s, 1H); 6.87 (dd, J=8.62, 2.19 Hz, 1H); 7.14 (d, J=2.05 Hz, 1H); 7.35-7.59 (m, 6H); 8.08 (br. s., 2H).

g) ethyl 3-(5-amino-2-phenyl-1H-indol-1-yl)propanoate

The process described above in Example 1f) was used, except that ethyl 3-bromopropanoate was used instead of ethyl 4-bromobutanoate.

ethyl 3-(5-nitro-2-phenyl-1H-indol-1-yl)propanoate
$^1$H NMR (DMSO-d$_6$) 1.02 (t, J=7.02 Hz, 3H); 2.61 (t, J=7.31 Hz, 2H); 3.88 (q, J=7.02 Hz, 2H); 4.57 (t, J=7.16 Hz, 2H); 6.83 (s, 1H); 7.46-7.65 (m, 5H); 7.80 (d, J=9.06 Hz, 1H); 8.08 (dd, J=9.06, 2.34 Hz, 1H); 8.57 (d, J=2.34 Hz, 1H).

ethyl 3-(5-amino-2-phenyl-1H-indol-1-yl)propanoate
$^1$H NMR (DMSO-d$_6$) 1.05 (t, J=7.16 Hz, 3H); 2.54 (br. s., J=7.50, 7.50 Hz, 2H); 3.90 (q, J=7.02 Hz, 2H); 4.36 (t, J=7.31 Hz, 2H); 4.55 (br. s., 2H); 6.24 (s, 1H); 6.57 (dd, J=8.62, 2.19 Hz, 1H); 6.70 (d, J=2.05 Hz, 1H); 7.21 (d, J=8.77 Hz, 1H); 7.34-7.55 (m, 5H).

h) ethyl (5-amino-2-phenyl-1H-indol-1-yl)acetate

The process described above in Example 1f) was used, except that ethyl 2-bromoacetate was used instead of ethyl 4-bromobutanoate.

ethyl (5-nitro-2-phenyl-1H-indol-1-yl)acetate:
$^1$H NMR (DMSO-d$_6$) 1.11 (t, J=7.02 Hz, 3H); 4.09 (q, J=7.02 Hz, 2H); 5.15 (s, 2H); 6.90 (d, J=0.58 Hz, 1H); 7.46-7.60 (m, 5H); 7.73 (d, J=9.35 Hz, 1H); 8.08 (dd, J=9.06, 2.34 Hz, 1H); 8.60 (d, J=2.34 Hz, 1H).

ethyl (5-amino-2-phenyl-1H-indol-1-yl)acetate:
$^1$H NMR (CDCl$_3$) 1.23 (t, J=7.16 Hz, 3H); 2.97 (br. s., 2H); 4.20 (q, J=7.02 Hz, 2H); 4.74 (s, 2H); 6.45 (s, 1H); 6.79 (dd, J=8.77, 2.05 Hz, 1H); 7.06 (s, 1H); 7.08 (d, J=5.85 Hz, 1H); 7.34-7.52 (m, 5H).

i) 1-[2-(dimethylamino)ethyl]-2-phenyl-1H-indol-5-amine

The process described above in Example 1f) was used, except that 2-chloro-N,N-dimethylethanamine hydrochloride was used instead of ethyl 4-bromobutanoate
N,N-dimethyl-2-(5-nitro-2-phenyl-1H-indol-1-yl)ethanamine:
$^1$H NMR (DMSO-d$_6$) 1.98 (s, 6H); 2.41 (t, J=6.87 Hz, 2H); 4.36 (t, J=6.87 Hz, 2H); 6.81 (s, 1H); 7.45-7.65 (m, 5H); 7.77 (d, J=9.06 Hz, 1H); 8.07 (dd, J=9.06, 2.34 Hz, 1H); 8.56 (d, J=2.34 Hz, 1H).
1-[2-(dimethylamino)ethyl]-2-phenyl-1H-indol-5-amine:
$^1$H NMR (DMSO-d$_6$) 2.00 (s, 6H); 2.38 (t, J=7.31 Hz, 2H); 4.13 (t, J=7.31 Hz, 2H); 4.52 (br. s., 2H); 6.23 (s, 1H); 6.57 (dd, J=8.62, 2.19 Hz, 1H); 6.69 (d, J=1.75 Hz, 1H); 7.19 (d, J=8.48 Hz, 1H); 7.35-7.58 (m, 5H).

l) 1-(2-methoxyethyl)-2-phenyl-1H-indol-5-amine

The process described above in Example 1f) was used, except that 1-bromo-2-methoxyethane was used instead of ethyl 4-bromobutanoate
1-(2-methoxyethyl)-5-nitro-2-phenyl-1H-indole
$^1$H NMR (DMSO-d$_6$) 3.04 (s, 3H); 3.53 (t, J=5.41 Hz, 2H); 4.44 (t, J=5.41 Hz, 2H); 6.83 (s, 1H); 7.46-7.66 (m, 5H); 7.79 (d, J=9.06 Hz, 1H); 8.06 (dd, J=9.06, 2.34 Hz, 1H); 8.57 (d, J=2.34 Hz, 1H).
1-(2-methoxyethyl)-2-phenyl-1H-indol-5-amine l) 4-(5-amino-2-phenyl-1H-indol-1-yl)butan-2-one The process described above in Example 10 was used, except that 4-chlorobutan-2-one was used instead of ethyl 4-bromobutanoate
4-(5-nitro-2-phenyl-1H-indol-1-yl)butan-2-one
$^1$H NMR (DMSO-d$_6$) 2.00 (s, 3H); 2.85 (t, J=7.50 Hz, 2H); 4.45 (t, J=7.50 Hz, 2H); 6.83 (d, J=0.58 Hz, 1H); 7.47-7.62 (m, 5H); 7.79 (d, J=9.35 Hz, 1H); 8.07 (dd, J=9.06, 2.34 Hz, 1H); 8.58 (d, J=2.34 Hz, 1H).
4-(5-amino-2-phenyl-1H-indol-1-yl)butan-2-one
$^1$H NMR (DMSO-d$_6$) 1.98 (s, 3H); 2.77 (t, J=7.68 Hz, 2H); 4.25 (t, J=7.68 Hz, 2H); 4.52 (br. s., 2H); 6.24 (s, 1H); 6.57 (dd, J=8.64, 2.06 Hz, 1H); 6.69 (d, J=1.92 Hz, 1H); 7.20 (d, J=8.51 Hz, 1H); 7.32-7.63 (m, 5H).

m) 2-(4-fluorophenyl)-1-(2-methoxyethyl)-1H-indol-5-amine

To a solution of 5-nitroindole (3.5 g; 21.6 mmol) in DMF (100 ml) was added Cs$_2$CO$_3$ (13.9 g; 42.6 mmol). The mixture thus obtained was stirred 1 h hour at room temperature then 1-bromo-2-methoxyethane (5.9 g; 42.6 mmol) was added dropwise. The resulting mixture was heated to 120° C. under stirring for 4 hours. After cooling, the mixture was poured into water (500 ml) and the crude product was filtered, dried under vacuum to give 1-(2-methoxyethyl)-5-nitro-1H-indole which was used in the following reaction without any further purification.
$^1$H NMR (DMSO-d$_6$) 3.21 (s, 3H); 3.68 (t, J=5.26 Hz, 2H); 4.43 (t, J=5.26 Hz, 2H); 6.75 (dd, J=3.22, 0.58 Hz, 1H); 7.62 (d, J=3.22 Hz, 1H); 7.70 (d, J=9.35 Hz, 1H); 8.02 (dd, J=9.06, 2.34 Hz, 1H); 8.56 (d, J=2.34 Hz, 1H).
To a suspension containing cesium acetate dried under vacuum overnight at 140° C. (7.3 g; 38 mmol) in N,N-dimethylacetamide (DMA, 10 ml), under an inert atmosphere, were added palladium acetate (0.22 g; 0.98 mmol), triphenylphosphine (1 g; 3.8 mmol), 1-(2-methoxyethyl)-5-nitro-1H-indole (4.2 g; 19.1 mmol) and 1-iodo-4-fluorobenzene (4.7 g; 21 mmol).
The reaction mixture was left under stirring at 140° C. under an inert atmosphere for 18 hours. The mixture was then cooled to room temperature, dichloromethane (100 ml) was added and the mixture thus obtained was filtered under vacuum through Celite.
The organic solution was transferred into a separating funnel, washed with H$_2$O (2×100 ml) and dried over Na$_2$SO$_4$.
The organic solvent was removed by evaporation under reduced pressure and the residue was purified by flash chromatography on silica gel (n-hexane/EtOAc, n-hexane 100→60%) to give 2-(4-fluorophenyl)-1-(2-methoxyethyl)-5-nitro-1H-indole (0.9 g), which was used without any further purification.
$^1$H NMR (DMSO-d$_6$) 3.05 (s, 3H); 3.53 (t, J=5.33 Hz, 2H); 4.41 (t, J=5.41 Hz, 2H); 6.83 (s, 1H); 7.32-7.44 (m, 2H); 7.62-7.73 (m, 2H); 7.79 (d, J=9.21 Hz, 1H); 8.06 (dd, J=9.06, 2.34 Hz, 1H); 8.57 (d, J=2.34 Hz, 1H).
To a suspension containing 2-(4-fluorophenyl)-1-(2-methoxyethyl)-5-nitro-1H-indole (0.9 g; 2.9 mmol) in ethanol absolute (100 ml) was added stannous chloride dihydrate (3.3 g; 14.6 mmol). The reaction mixture was left under stirring at 75° C. for 48 hours. The mixture was then cooled to room temperature, the solvent partially evaporated under reduced pressure and poured in water (100 ml) and ice. NaHCO$_3$ (saturated solution) was added to pH 8 and the mixture was left under stirring for 20 minutes. The solution was transferred into a separating funnel, and extracted with ethyl acetate (2×50 ml). The organic phases were combined, and the resulting organic phase was washed with H$_2$O (2×100 ml) and dried over Na$_2$SO$_4$.
The organic solvent was removed by evaporation under reduced pressure and the residue was purified by flash chromatography on silica gel (n-hexane/EtOAc, n-hexane 100→60%) to give 2-(4-fluorophenyl)-1-(2-methoxyethyl)-1H-indol-5-amine (0.7 g), which was used without any further purification.
$^1$H NMR (DMSO-d$_6$) 3.07 (s, 3H); 3.51 (t, J=5.70 Hz, 2H); 4.18 (t, J=5.85 Hz, 2H); 4.53 (br. s., 2H); 6.22 (s, 1H); 6.56 (dd, J=8.62, 2.19 Hz, 1H); 6.69 (d, J=1.46 Hz, 1H); 7.22 (d, J=8.77 Hz, 1H); 7.30 (t, J=8.92 Hz, 2H); 7.59 (dd, J=9.06, 5.55 Hz, 2H).

n) 3-(5-amino-2-phenyl-1H-indol-1-yl)propyl acetate

To a solution containing ethyl 3-(5-nitro-2-phenyl-1H-indol-1-yl)propanoate (prepared as described in example 1 g) (2.1 g; 6.2 mmol) in THF (20 ml) sodium borohydride (0.98 g, 24.8 mmol) and EtOH absolute (25 ml) were added; the reaction mixture was left under stirring at room temperature for 18 hours. Then water (5 ml) and HCl 2N were added to pH 6. The solution was transferred into a separating funnel, and extracted with ethyl acetate (2×50 ml). The organic phases were combined, and dried over Na$_2$SO$_4$. The solvent was removed by evaporation under reduced pressure and the residue was purified by flash chromatography on silica gel (n-hexane/EtOAc, n-hexane 100→70%) to give 3-(5-nitro-2-phenyl-1H-indol-1-yl)propan-1-ol (1.5 g), which was used without any further purification.
$^1$H NMR (CDCl$_3$) 1.81-1.93 (m, J=6.58, 6.58, 6.43, 6.14 Hz, 2H); 3.36 (t, J=5.70 Hz, 2H); 3.50 (br. s., 1H); 4.38 (t, J=7.02 Hz, 2H); 6.69 (s, 1H); 7.28-7.61 (m, 6H); 8.06 (dd, J=9.06, 2.34 Hz, 1H); 8.55 (d, J=2.05 Hz, 1H).
To a solution containing ethyl 3-(5-nitro-2-phenyl-1H-indol-1-yl) propan-1-ol (2.2 g; 7.4 mmol) and triethylamine (1.24 ml; 8.9 mmol) in CH$_2$Cl$_2$ (20 ml), acetyl chloride (0.6 ml; 8.9 mmol) was added dropwise; the reaction mixture was left under stirring at room temperature for 2 hours. Then water (20 ml) and NaHCO$_3$ (saturated solution) were added to pH 7. The biphasic solution was transferred into a separating funnel extracted with CH$_2$Cl$_2$ (2×50 ml). The organic phases were combined, washed with brine (2×100 ml) and dried over Na$_2$SO$_4$. The solvent was removed by evaporation under reduced pressure to give 3-(5-nitro-2-phenyl-1H-indol-1-yl) propyl acetate (1.5 g), which was used without any further purification.

$^1$H NMR (DMSO-d$_6$) 1.79 (s, 3H); 1.86 (qd, J=6.63, 6.43 Hz, 2H); 3.75 (t, J=5.99 Hz, 2H); 4.41 (t, J=7.16 Hz, 2H); 6.85 (s, 1H); 7.47-7.64 (m, 5H); 7.79 (d, J=9.06 Hz, 1H); 8.08 (dd, J=9.06, 2.34 Hz, 1H); 8.59 (d, J=2.05 Hz, 1H).

To a suspension of 10% Pd/C (87 mg, 0.08 mmol) in 95° ethanol (100 ml) a solution of 3-(5-nitro-2-phenyl-1H-indol-1-yl)propyl acetate (2.76 g; 8 mmol) in 95° ethanol (200 ml) was added and the mixture underwent hydrogenation in a Parr hydrogenator (H$_2$, 30 psi) for 4 hours.

The residue was filtered under vacuum through Celite to remove the catalyst and the solvent evaporated to give crude 3-(5-amino-2-phenyl-1H-indol-1-yl)propyl acetate which was used without any further purification.

o) 2-(5-amino-2-phenyl-1H-indol-1-yl)ethyl acetate

The process described above in Example 1n) was used, except that ethyl (5-nitro-2-phenyl-1H-indol-1-yl)acetate (prepared as described in example 1h) was used instead of 3-(5-nitro-2-phenyl-1H-indol-1-yl)propanoate.

2-(5-nitro-2-phenyl-1H-indol-1-yl)ethanol $^1$H NMR (DMSO-d$_6$) 3.63 (t, J=5.85 Hz, 2H); 4.32 (t, J=5.85 Hz, 2H); 6.46 (br. s., 1H); 6.83 (s, 1H); 7.43-7.71 (m, 5H); 7.77 (d, J=9.06 Hz, 1H); 8.06 (dd, J=9.06, 2.34 Hz, 1H); 8.57 (d, J=2.34 Hz, 1H).

ethyl 2-(5-nitro-2-phenyl-1H-indol-1-yl)acetate $^1$H NMR (DMSO-d$_6$) 1.70 (s, 3H); 4.16 (t, J=5.26 Hz, 2H); 4.57 (t, J=5.26 Hz, 2H); 6.83 (s, 1H); 7.35-7.70 (m, 5H); 7.81 (d, J=9.35 Hz, 1H); 8.09 (dd, J=9.35, 2.34 Hz, 1H); 8.58 (d, J=2.34 Hz, 1H).

p) 2-cyclohexyl-1-ethyl-1H-indol-5-amine

To a solution containing 2-iodo-4-nitroaniline (25 g; 95 mmol) and triethylamine (43 ml; 312 mmol) in CH$_2$Cl$_2$ (250 ml), a solution containing methanesulphonyl chloride (36 g; 312 mmol) was added dropwise. The reaction mixture was left under stirring at room temperature for 18 hours, then NH$_4$Cl (saturated solution) was added (250 ml). The biphasic solution was transferred into a separating funnel, the organic phase was separated, dried over Na$_2$SO$_4$ and the solvent was removed by evaporation under reduced pressure. The residue was suspended in EtOH (200 ml) and heated under stirring until a yellow solid precipitated. The crude product was filtered, washed with EtOH (750 ml), and dried under vacuum to give N-(2-iodo-4-nitrophenyl)-N-(methylsulfonyl)methanesulfonamide (32 g) which was used in the following reaction without any further purification.

$^1$H NMR (DMSO-d$_6$) 3.68 (s, 6H); 7.93 (d, J=8.77 Hz, 1H); 8.29 (dd, J=8.48, 2.34 Hz, 1H); 8.73 (d, J=2.63 Hz, 1H).

To a mixture containing N-(2-iodo-4-nitrophenyl)-N-(methylsulfonyl)methanesulfonamide (31 g; 75 mmol) in EtOH (230 ml), water (115 ml) and LiOH (9 g; 375 mmol) were added. The reaction mixture was refluxed for 2 hours, then cooled to room temperature, the solvent evaporated under reduced pressure. NH$_4$Cl (saturated solution, 250 ml) was added and the mixture was stirred until a yellow solid precipitated. The crude product was filtered and dried under vacuum to give N-(2-iodo-4-nitrophenyl)methanesulfonamide (24 g) which was used in the following reaction without any further purification.

$^1$H NMR (DMSO-d$_6$) 3.01 (s, 3H); 7.41 (d, J=9.06 Hz, 1H); 8.10 (dd, J=9.21, 2.78 Hz, 1H); 8.53 (d, J=2.92 Hz, 1H); 9.55 (br. s., 0H).

To a mixture containing N-(2-iodo-4-nitrophenyl)methanesulfonamide (13.5 g; 39.5 mmol), triethylamine (17.9 ml; 129 mmol), ethynylcyclohexane (8.55 g; 79 mmol) in DMF (60 ml), CuI (1.5 g; 7.9 mmol) and dichlorobis(triphenylphosphine)palladium(II) [Cl$_2$(PPh$_3$)$_2$Pd] (2.77 g; 3.95 mmol) were added. The reaction mixture was left under stirring at 70° C. for 18 hours. After cooling to room temperature, EtOAc (100 ml) was added, the inorganic precipitate was filtered off and the solution was transferred into a separating funnel and washed with NaHCO$_3$ (saturated solution, 3×200 ml) and water (2×150 ml). The organic phase was dried over Na$_2$SO$_4$, the solvent was removed by evaporation under reduced pressure. The so obtained crude product was crystallized (isopropyl ether) to give 2-cyclohexyl-1-(methylsulfonyl)-5-nitro-1H-indole (11.7 g)

$^1$H NMR (DMSO-d$_6$) 1.14-1.53 (m, 5H); 1.62-1.93 (m, 3H); 2.02-2.20 (m, 2H); 3.08-3.27 (m, 1H); 3.46 (s, 3H); 6.87 (s, 1H); 8.09 (d, J=9.10 Hz, 1H); 8.17 (dd, J=9.10, 2.05 Hz, 1H); 8.52 (d, J=2.05 Hz, 1H).

To a solution containing 2-cyclohexyl-1-(methylsulfonyl)-5-nitro-1H-indole (5.8 g; 18 mmol) in THF (50 ml), tetrabutylammonium fluoride (1M solution in THF; 18 ml; 18 mmol) was added dropwise. The reaction mixture was refluxed for 18 hours, then cooled to room temperature. Water (50 ml) and EtOAc (50 ml) were added, the biphasic solution was transferred into a separating funnel, the organic layer separated and dried over Na$_2$SO$_4$, and the solvent was removed by evaporation under reduced pressure. The residue was purified by flash chromatography on silica gel (n-hexane/EtOAc, n-hexane 100→480%) to give 2-cyclohexyl-5-nitro-1H-indole (3.2 g), which was used without any further purification.

$^1$H NMR (DMSO-d$_6$) 1.12-1.58 (m, 5H); 1.64-1.87 (m, 3H); 1.95-2.12 (m, 2H); 2.67-2.85 (m, 1H); 6.41 (d, J=1.98 Hz, 1H); 7.43 (d, J=8.92 Hz, 1H); 7.92 (dd, J=8.92, 2.31 Hz, 1H); 8.43 (d, J=2.31 Hz, 1H); 11.66 (br. s., 1H).

To a solution of 2-cyclohexyl-5-nitro-1H-indole (5 g; 20.5 mmol) in DMF (100 ml) sodium hydride (50% suspension) (1 g, 20.5 mmol) was added; the mixture was left under stirring for 30 minutes, then ethyl iodide (2.5 ml; 30.8 mmol) in DMF (10 ml) was added dropwise and the resulting mixture was left under stirring at room temperature for 18 hours. The reaction mixture was poured in NaHCO$_3$ (saturated solution, 100 ml) and stirred for 30 minutes. The solid was filtered under vacuum to give 2-cyclohexyl-1-ethyl-5-nitro-1H-indole (4.8 g) which was used without any further purification.

$^1$H NMR (DMSO-d$_6$) 1.16-1.56 (m, 5H); 1.29 (t, J=7.09 Hz, 3H); 1.67-1.89 (m, 3H); 1.90-2.05 (m, 2H); 2.69-2.86 (m, 1H); 4.28 (q, J=7.16 Hz, 2H); 6.52 (s, 1H); 7.62 (d, J=9.06 Hz, 1H); 7.96 (dd, J=9.06, 2.34 Hz, 1H); 8.45 (d, J=2.34 Hz, 1H).

To a suspension of 10% Pd/C (380 mg, 0.36 mmol) in 95° ethanol (50 ml) a solution of 2-cyclohexyl-1-ethyl-5-nitro-1H-indole (4.8 g; 18 mmol) in 95° ethanol (100 ml) was added and the mixture underwent hydrogenation in a Parr hydrogenator (H$_2$, 30 psi) for 4 hours. The residue was filtered under vacuum through Celite to remove the catalyst and the solvent evaporated to give crude 2-cyclohexyl-1-ethyl-1H-indol-5-amine (4 g) which was used without any further purification.

Monoisotopic mass=242.18; GC/MS (M)$^+$ m/z=242.

q) 2-phenethyl-1-ethyl-1H-indol-5-amine

To a solution of 2-iodo-4-nitroaniline (1.02 g, 3.86 mmol) in dichloromethane (10 ml), has been added under stirring triethylamine (1.77 ml, 12.7 mmol). To this mixture, a solution of methanesulphonyl chloride (0.98 ml, 12.7 mmol) in dichloromethane (2 ml) has been added dropwise, very slowly and in an ice-bath. The mixture so obtained was left under stirring at room temperature overnight. The day after, the reaction mixture was neutralized with a saturated aqueous solution of $NH_4Cl$. The organic phase was separated, and, after evaporation of the solvent, the residue has been washed with ethanol and filtered to give N-(2-iodo-4-nitrophenyl)-N-(methylsulfonyl)-methanesulfonamide as yellow solid.

N-(2-iodo-4-nitrophenyl)-N-(methylsulfonyl)methanesulfonamide:
$^1$H-NMR (DMSO-$d_6$): 8.73 (d, J=2.6 Hz, 1H); 8.29 (dd, J=8.8, 2.6 Hz, 1H); 7.93 (d, J=8.8 Hz, 1H); 3.68 (s, 6H).

LiOH (0.21 mg, 8.9 mmol) in a mixture ethanol/water 2/1 (18 ml) was added to a solution of N-(2-iodo-4-nitrophenyl)-N-(methylsulfonyl)methanesulfonamide (0.75 g, 1.78 mmol). The reaction mixture was refluxed for two hours. After cooling at room temperature, the reaction mixture was neutralized with $H_2O$, $NH_4Cl$ and HCl 2N, then ethanol was eliminated, and the aqueous phase was extracted with ethyl acetate (3×20 ml). The organic solvent was removed by evaporating under reduced pressure to give N-(2-iodo-4-nitrophenyl)methanesulfonamide without further purification.

N-(2-iodo-4-nitrophenyl)methanesulfonamide:
$^1$H-NMR (DMSO-$d_6$): 9.53 (br. s., 1H); 8.59 (d, J=2.2 Hz, 1H); 8.19 (dd, J=8.8, 2.7, 1H); 7.55 (d, J=8.8, 1H); 3.14 (s, 3H).

CuI (0.06 g, 0.34 mmol) previously maintained in oven for at least 48 hours, bis(triphenylphosphino)palladium dichloride (0.2 g, 0.17 mmol), triethylamine (1.1 ml, 7.82 mmol) and 4-phenyl-1-butyne (0.44 g, 3.4 mmol) was added to a solution of N-(2-iodo-4-nitrophenyl)methanesulfonamide (0.6 g, 1.7 mmol) in anhydrous DMF (20 ml) kept under nitrogen atmosphere. The reaction mixture was left under stirring overnight. Next morning, after cooling, the reaction mixture was poured in $H_2O$ and ice (200 ml) leaving under stirring for some hours. After filtration, a brown solid was recovered, recrystallized from ethyl acetate/hexane 1:1, and then from iPrOH/EtOH 9:1. The residue was filtered to give 1-(methylsulfonyl)-5-nitro-2-(2-phenethyl)-1H-indole.

1-(methylsulfonyl)-5-nitro-2-(2-phenethyl)-1H-indole:
$^1$H-NMR (DMSO-$d_6$): 8.53 (d, J=2.0 Hz, 1H); 8.18 (dd, J=8.4, 2.5, 1H); 8.10 (d, 1H); 7.29 (m, 5H); 6.91 (s, 1H); 3.52 (s, 3H); 3.29 (m, 2H); 3.05 (m, 2H).

Tetrabutyl ammonium fluoride (TBAF, 0.37 ml, 1.29 mmol) was added to a solution of 1-(methylsulfonyl)-5-nitro-2-(2-phenethyl)-1H-indole (0.25 g, 0.95 mmol) in THF (5 ml). The reaction mixture was refluxed overnight under stirring. The next morning, after cooling, the reaction mixture was poured in $H_2O$, and kept under stirring overnight. After filtration, the solid was purified with flash chromatography on silica gel (n-hexane/EtOAc, n-hexane 90→80%) to give 2-phenethyl-5-nitro-1H-indole.

2-phenethyl-5-nitro-1H-indole:
$^1$H NMR (300 MHz, DMSO-d6) δ 11.76 (br. s., 1H), 8.42 (d, J=2.31 Hz, 1H), 7.93 (dd, J=2.31, 8.92 Hz, 1H), 7.45 (d, J=8.92 Hz, 1H), 7.11-7.34 (m, 5H), 6.45 (s, 1H), 2.97-3.15 (m, 4H)

A 60% dispersion of NaH (0.5 g, 2.02 mmol) was added to a solution of 2-phenethyl-5-nitro-1H-indole (0.16 g, 0.6 mmol) in DMF (30 ml). The reaction mixture was kept under stirring for 30 minutes. Then, ethyl iodide (0.15 ml, 1.9 mmol) was added, and the mixture was left under stirring overnight at room temperature. The next morning, the mixture was poured in $H_2O$ left under stirring overnight, obtaining a precipitate which was filtered to give 2-phenethyl-1-ethyl-5-nitro-1H-indole.

2-phenethyl-1-ethyl-5-nitro-1H-indole:
$^1$H NMR (300 MHz, DMSO-d6) δ 8.46 (d, J=2.05 Hz, 1H), 7.97 (dd, J=2.34, 9.06 Hz, 1H), 7.62 (d, J=9.06 Hz, 1H), 7.13-7.40 (m, 5H), 6.58 (s, 1H), 4.26 (q, J=7.31 Hz, 2H), 2.99-3.18 (m, 4H), 1.25 (t, J=7.20 Hz, 3H)

$SnCl_2$ (1.2 g, 6.3 mmol) was added to a solution of 2-phenethyl-1-ethyl-5-nitro-1H-indole (0.17 g, 0.57 mmol) in THF (50 ml). The mixture was kept under stirring at 70° C. overnight. After cooling, the mixture was poured in $H_2O$, neutralized with $NaHCO_3$, and extracted with ethyl acetate (3×50 ml). After evaporation of the solvent under reduced pressure, the solid was purified on a chromatographic column using $CHCl_3$ as eluent to give 2-phenethyl-1-ethyl-1H-indol-5-amine.

2-phenethyl-1-ethyl-1H-indol-5-amine:
$^1$H NMR (300 MHz, DMSO-$d_6$) δ 7.25-7.37 (m, 4H), 7.15-7.25 (m, 1H), 7.11 (d, J=8.48 Hz, 1H), 6.72 (d, J=2.05 Hz, 1H), 6.53 (dd, J=2.19, 8.62 Hz, 1H), 6.02 (s, 1H), 5.46 (br. s., 2H), 4.05 (q, J=7.11 Hz, 2H), 2.81-3.15 (m, 4H), 1.18 (t, J=7.16 Hz, 3H)

r) 2-benzyl-1-ethyl-1H-indol-5-ammina

The intermediate compound r) was prepared with a procedure similar to that described for the intermediate compound q) by using 3-phenyl-1-propyne (0.16 g, 1.4 mmol) instead of 4-phenyl-1-butyne.

2-benzyl-1-(methanesulfonyl)-5-nitro-1H-indole:
$^1$H-NMR (DMSO-$d_6$): 8.54 (d, J=2.3 Hz, 1H); 8.17 (m, 1H); 8.08 (m, 1H); 7.35 (m, 5H); 6.53 (s, 1H); 4.37 (s, 2H); 3.37 (s, 3H).

2-benzyl-5-nitro-1H-indole:
$^1$H-NMR (DMSO-$d_6$): 11.74 (bs, 1H); 8.44 (d, J=2.3 Hz, 2H); 7.92 (dd, J=8.9, 2.3 Hz, 1H); 7.44 (d, J=8.9, 1H); 7.32 (m, 4H); 7.24 (m, 1H); 6.44 (s, 1H); 4.12 (s, 2H).

2-benzyl-1-ethyl-5-nitro-1H-indole:
$^1$H-NMR (DMSO-$d_6$): 8.48 (d, J=2.3 Hz, 1H); 7.98 (dd, J=9.1, 2.3 Hz, 1H); 7.60 (d, J=9.1 Hz, 1H); 7.30 (m, 5H); 6.43 (s, 1H); 4.22 (m, 4H); 1.09 (t, J=7.2 Hz, 3H).

2-benzyl-1-ethyl-1H-indol-5-amine:
$^1$H-NMR (DMSO-$d_6$): 7.22 (m, 5H); 7.04 (d, J=8.5 Hz, 1H); 6.84 (d, J=2.3 Hz, 1H); 6.59 (dd, J=8.5, 2.3 Hz, 1H); 6.05 (s, 1H); 4.05 (s, 2H); 3.94 (q, J=7.2 Hz, 2H); 3.22 (bs, 2H); 1.10 (t, J=7.2 Hz, 3H).

s) 5-amino-1-(3-triisopropylsilanyloxypropyl)-1H-indol-2-carboxylic acid phenylamide $N_2H_4$*$H_2O$ (25 ml) was added dropwise to a solution of 1-fluoro-4-nitrobenzene. The mixture was kept under stirring, at first at room temperature for 3 hours, and then under reflux for 1 hour. After cooling, the resulting precipitate was filtered and washed with $H_2O$ to give 4-nitrophenylhydrazine which was used in the next reaction without any further purification.

4-nitrophenylhydrazine: M/z (APCI$^+$) 154 (MH$^+$)

A suspension in water (150 ml) of 4-nitrophenylhydrazine (15 g, 23 mmol) and 2-oxo-propionic acid ethyl ester (12 g, 100 mmol) was left under stirring at room temperature for 6 hours. The obtained precipitate was filtered and washed to give the ethyl ester of the 2-[(4-nitrophenyl)-hydrazono]-propionic acid.

¹H-NMR (DMSO-d₆): 10.45 (s, 1H); 8.21-8.15 (m, 2H); 7.42-7.36 (m, 2H); 4.28-4.15 (m, 2H); 2.15 (s, 3H); 1.36-1.22 (m, 3H).

Polyphosphoric acid (PPA, 50 g) was added to a solution of ethyl ester of the 2-[(4-nitrophenyl)-hydrazono]-propionic acid (6 g, 23 mmol) in toluene (70 ml). The mixture was refluxed for 3 hours, then was cooled at 0-10° C., and added with NH₄Cl until pH 8-9. The mixture was extracted with ethyl acetate (EtOAc), and then the solvent was removed by evaporation under reduced pressure. The residue was purified by flash chromatography on silica gel (n-hexane/EtOAc, 80/20) and crystallized with CH₂Cl₂ to give the ethyl ester of 5-nitro-1H-indole-2-carboxylic acid.

Ethyl ester of 5-nitro-1H-indole-2-carboxylic acid:
¹H-NMR (DMSO-d₆): 12.55 (s, 1H); 8.73 (s, 1H); 8.14 (d, 1H); 7.62 (d, 1H); 7.45 (s, 1H); 4.45-4.32 (m, 2H); 1.43-1.30 (m, 3H).

Anhydrous K₂CO₃ (2.36 g, 17.1 mmol), 18-crown-6 (1.14 g, 4.28 mmol) and 3-triisopropylsilanyloxypropyl bromide (3.78 g, 12.82 mmol) were added to a solution of ethyl ester of 5-nitro-1H-indole-2-carboxylic acid (2 g, 8.85 mmol) in anhydrous acetonitrile (50 ml). The mixture was heated at 80° C. for 4 hours. After evaporation of the solvent under reduced pressure, water was added, and the resulting mixture was extracted with dichloromethane. After evaporation of the solvent under reduced pressure, the solid was purified by flash chromatography on silica gel (n-hexane/EtOAc, 50/10) to give the ethyl ester of 5-nitro-1-(triisopropylsilaniloxypropyl)-1H-indole-2-carboxylic acid: M/z (APCI⁺) 449 (MH⁺)

The ethyl ester of 5-nitro-1-(triisopropylsilaniloxypropyl)-1H-indole-2-carboxylic acid (2.76 g, 6.2 mmol) was dissolved in a solution of KOH 5% in EtOH/H₂O 1/1 (80 ml) and left under stirring at room temperature for 16 hours. Ethanol was then evaporated, and 1N HCl was added to the solution until to pH 5. The solution was then extracted with EtOAc. After evaporation of the solvent under reduced pressure, the solid was washed with n-hexane/dichloromethane 10/1 and filtered to give the 5-nitro-1-(triisopropylsilaniloxypropyl)-1H-indole-2-carboxylic acid.

5-nitro-1-(triisopropylsilaniloxypropyl)-1H-indole-2-carboxylic acid:
M/z (APCI⁺) 421 (MH⁺)

A mixture of 5-nitro-1-(tri isopropylsilaniloxypropyl)-1H-indole-2-carboxylic acid (0.448 g, 1.065 mmol), O-benzotriazol-1-yl-N,N,N',N'-tetramethyluronium tetrafluoroborate (TBTU) (0.478 g, 1.49 mmol) and triethylamine (0.22 ml, 1.59 mmol) in anhydrous acrylonitrile (14 ml) was kept under stirring at room temperature for 30 minutes. Aniline (0.109 g, 1.175 mmol) was added to this mixture. The mixture was left at 50°-55° C. for about 3 hours, and then diluted with H₂O and extracted with ethyl acetate (EtOAc). After evaporation of the solvent under reduced pressure, the obtained solid was purified by flash chromatography on silica gel (n-hexane/EtOAc, 50/10) to give phenylamide of 5-nitro-1-(triisopropylsilaniloxypropyl)-1H-indole-2-carboxylic acid:
M/z (APCI⁺) 496 (MH⁺)

A catalytic amount of 10% Pd/C was added to a solution of phenylamide of 5-nitro-1-(triisopropylsilaniloxypropyl)-1H-indole-2-carboxylic acid (0.323 g, 0.65 mmol) in MeOH (100 ml), and the mixture was hydrogenated at 29 psi for 12 hours. The solution was filtered through Celite™ and the filtrate was evaporated under reduced pressure to give a solid used without any further purification.

Phenylamide of 5-amino-1-(triisopropylsilaniloxypropyl)-1H-indole-2-carboxylic acid: M/z (APCI⁺) 466 (MH⁺).

EXAMPLE 2

Preparation of Compounds of the Invention a) Example of a first variant of the preparation process:

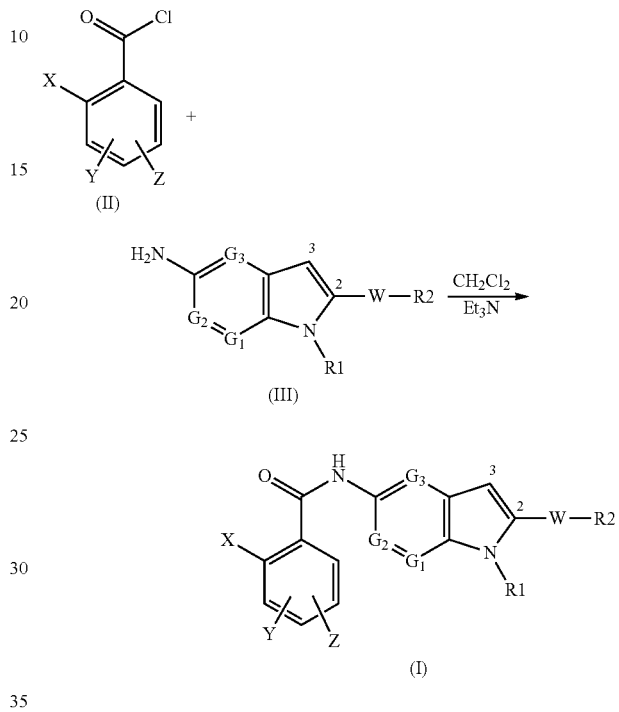

To a solution of a 5-amino(aza)indole (III) (2 mmol) in dichloromethane (10 ml) was added triethylamine (2.2 mmol), followed by dropwise addition of an acyl chloride (II) (2.2 mmol) dissolved in dichloromethane (10 ml). Once the additions were complete, the mixture was left under stirring at room temperature for 20 hours. Water (50 ml) was then added and the organic phase was separated out and dried over Na₂SO₄. The solution was evaporated under reduced pressure. The crude product obtained was purified to give compound of formula (I) in which X, Y, Z, G1, G2, G3, R1, W and R2 have the meanings given above.

b) Example of a second variant of the preparation process:

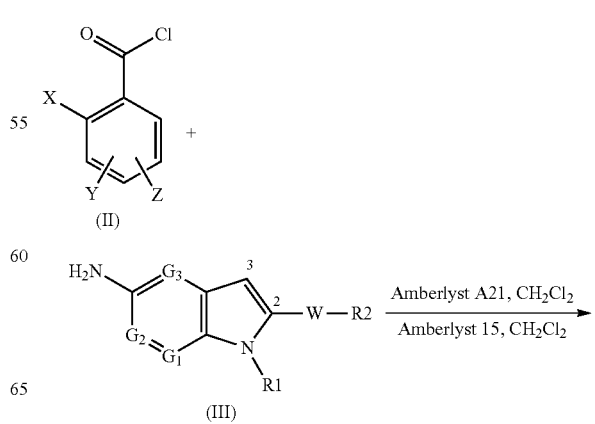

-continued

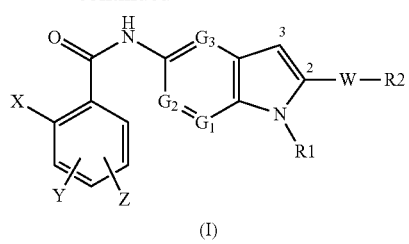

(I)

To a suspension of 5-amino(aza)indole (III) (0.9 mmol) were added Amberlyst A21 resin (0.9 g) in dichloromethane (3 ml) and an acyl chloride (II) (0.28 mmol) in dichloromethane (3 ml). The mixture was left under stirring for 20 hours. The Amberlyst A21 resin was then removed by filtration and washed with dichloromethane (5 ml). The organic phases were combined, diluted with dimethylformamide (1 ml) and stirred with Amberlyst 15 resin (0.9 g) for 5 hours. This treatment was repeated twice. The Amberlyst 15 resin was removed by filtration and the solution was evaporated under centrifuge to give compound of formula (I) in which X, Y, Z, G1, G2, G3, R1, W and R2 have the meanings given above.

c) Example of a third variant of the preparation process:

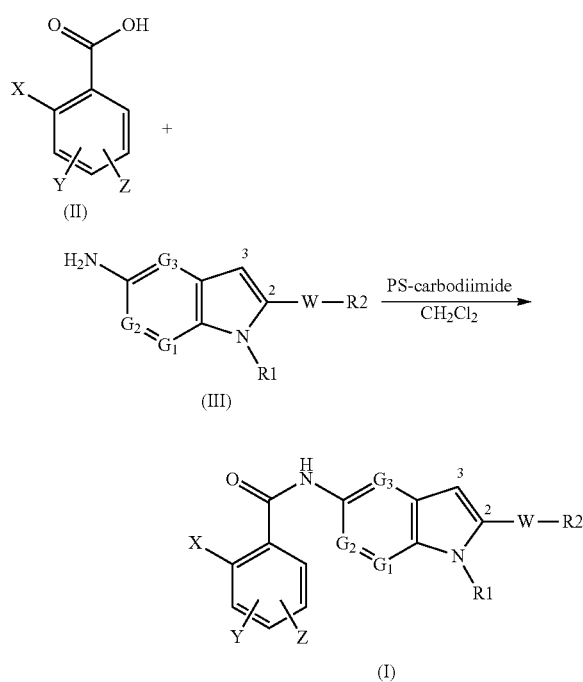

Under an inert atmosphere, a benzoic acid (II) (0.67 mmol) and a 5-amino(aza)indole (III) (0.45 mmol) were dissolved in dichloromethane (8 ml) and dimethylformamide (0.8 ml). After leaving the mixture stirring at room temperature for 10 minutes, PS-carbodiimide resin (0.73 g) was added.

After leaving the reaction mixture stirring for 20 hours, the resin was removed by filtration and washed with dichloromethane (2×5 ml). The solution was evaporated under centrifugation to give compound of formula (I) in which X, Y, Z, G1, G2, G3, R1, W and R2 have the meanings given above.

d) Example of a fourth variant of the preparation process:

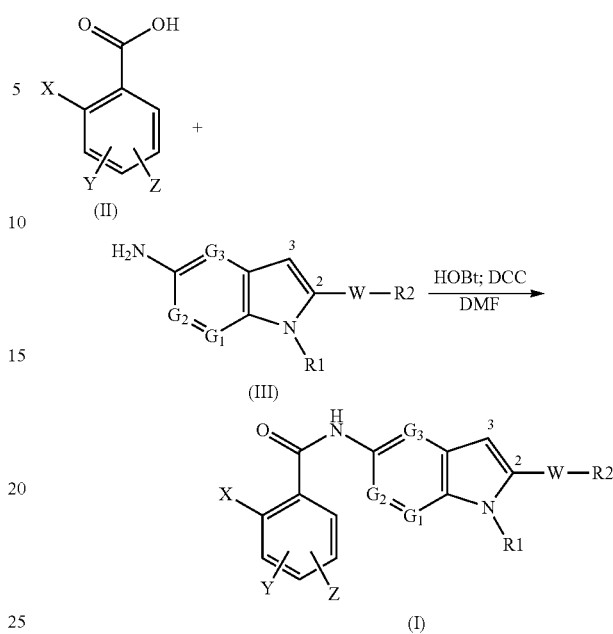

To a solution of a benzoic acid (II) (10 mmol) in dimethylformamide (40 ml) with stirring at 0° C., 1-hydroxybenzotriazol (HOBt) (10 mmol) and dicyclohexylcarbodiimide (DCC) (10 mmol) were added. The mixture was left under stirring at 0° C. for 30 minutes and a 5-amino(aza)indole (III) (9 mmol) dissolved in dimethylformamide (20 ml) was added.

The mixture was left under stirring at 0° C. for a further 30 minutes, and then at room temperature for 18 hours. The mixture was filtered, 2N hydrochloric acid was added to pH 2, and the precipitate thus formed was filtered off and purified to give compound of formula (I) in which X, Y, Z, G1, G2, G3, R1, W and R2 have the meanings given above.

e) Example of a fifth variant of the preparation process:

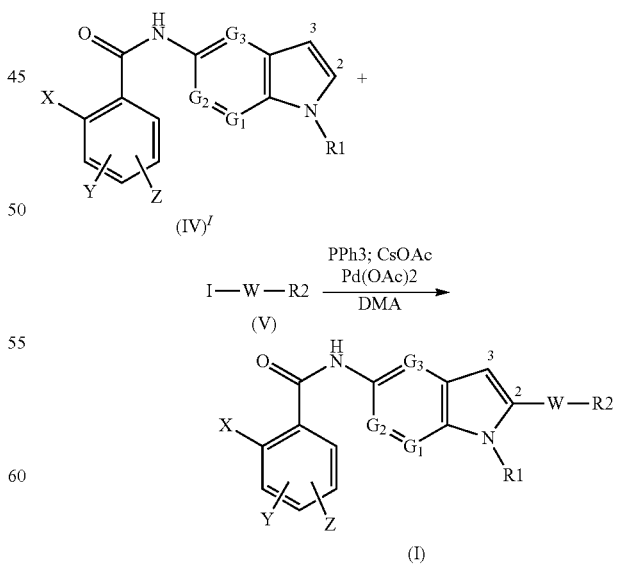

To a suspension of cesium acetate dried under vacuum overnight at 140° C. (6.02 mmol) in N,N-dimethylacetamide (DMA) (3 ml), under an inert atmosphere, were added palladium acetate (0.017 mmol), triphenylphosphine (0.067 mmol), 5-amino(aza)indole (IV)$^I$ (3.35 mmol) and an aryl iodide (V) (3.68 mmol).

The reaction mixture was left under stirring at 140° C. under an inert atmosphere for 18 hours. The reaction mixture was cooled to room temperature, dichloromethane (50 ml) was added and the resulting mixture was filtered under vacuum through Celite. The filtered organic solution was transferred into a separating funnel. The organic phase was washed with H$_2$O (2×50 ml), dried over Na$_2$SO$_4$ and evaporated under reduced pressure.

The residue was purified to give compound of formula (I) in which X, Y, Z, G1, G2, G3, R1, W and R2 have the meanings given above.

f) Example of solid phase preparation using a PL-FMP resin:

The following example of solid phase preparation by using a preparative resin is given with specific reference to compounds of the present invention wherein the above mentioned G1, G2, G3 groups are CH and R1 is SO2R$^I$ and X, Y, Z, W, R2 and R$^I$ have the meanings given above. Additionally, the following example comprises steps 1 and 2 to prepare the starting compound B1 of the process of the present invention because intermediate A1 is first prepared in situ without separation from the preparative resin.

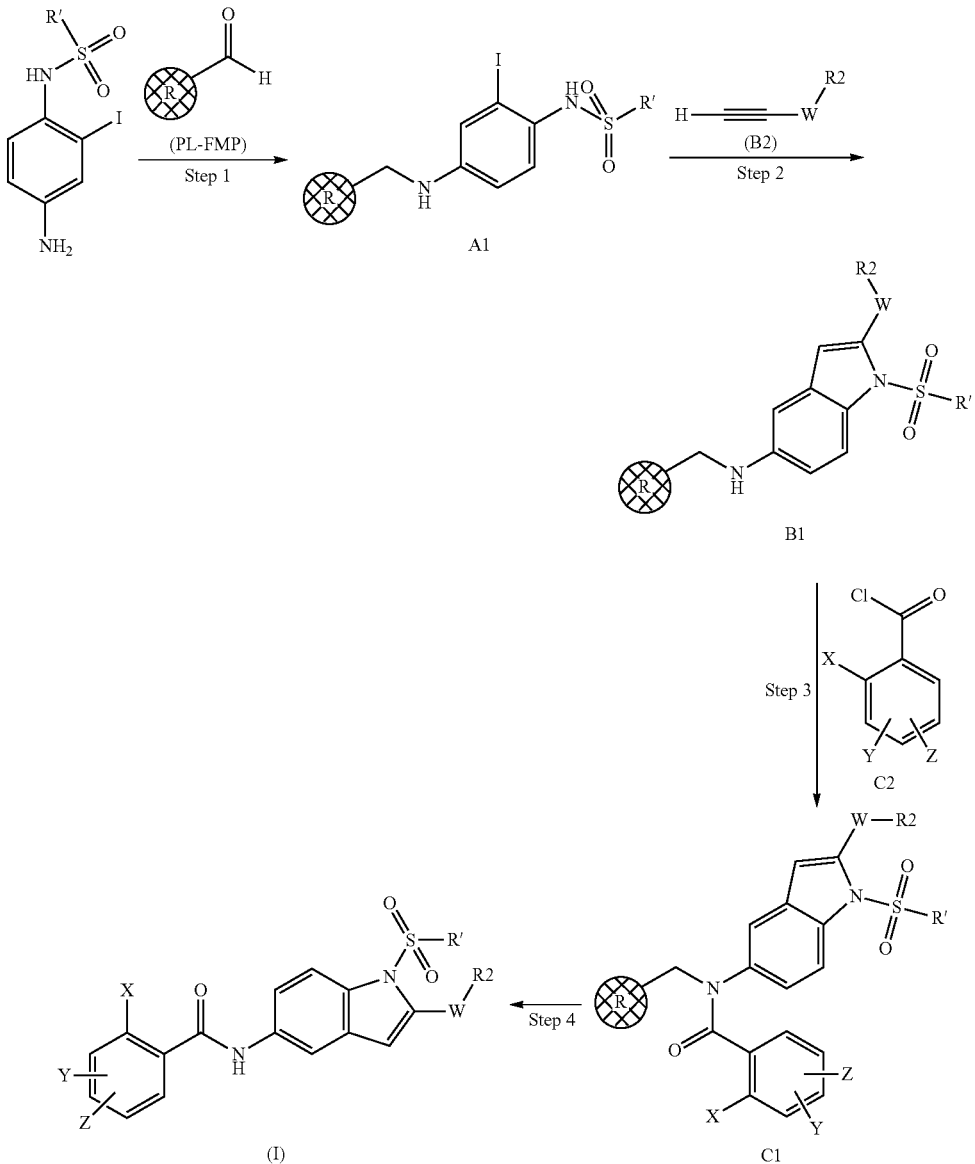

Step (1): 15 g of PL-FMP resin (0.9 mmol/g) in a solution 1% AcOH in DMF (300 ml) was stirred at room temperature for 2 h. Then, N-(4-amino-2-iodophenyl)alkylsulfonamide (54 mmol) and 11.5 g of sodium triacetoxyborohydride (54 mmol) were added. PL-FMP Resin (manufactured by Polymer Laboratories, UK) is an aldehyde-based resin suitable for attachment of amines via reductive amination. The mixture was stirred at room temperature for 24 h, then the resin was filtered and washed with DMF (3×150 ml), DMF/MeOH in a 1/1 volume ratio (3×150 ml), MeOH (3×150 ml), CH$_2$Cl$_2$/MeOH in a 1/1 volume ratio (3×100 ml), and CH$_2$Cl$_2$ (3×100 ml). The resin was dried under vacuum at room temperature to give 18.3 g of resin (A1) which was used without any further purification.

Step (2): 1.172 g of resin (A1) (0.8 mmol, theoretical) were added to a mixture of DMF (10 ml), the B2 alkyne (5 mmol), CuI (32 mg, 0.17 mmol), 58 mg of dichlorobis(triphenylphosphine)palladium(11) [Cl$_2$(PPh$_3$)$_2$Pd] (0.8 mmol) and 2 ml of triethylamine (22 mmol). The mixture was heated at 70° C. and stirred for 48 h.

The reaction was quenched by cooling to room temperature. The resin was filtered and washed with DMF (3×10 ml), DMF/H$_2$O in a 95/5 volume ratio (3×10 ml), DMF/H$_2$O in a 90/10 volume ratio (3×10 ml), DMF/H$_2$O in a 80/20 volume ratio (3×10 ml), DMF/H$_2$O in a 50/50 volume ratio (3×10 ml), DMF (3×10 ml), DMF/MeOH in a 50/50 volume ratio (3×10 ml), MeOH (3×10 ml), MeOH/CH$_2$Cl$_2$ in a 50/50 volume ratio (3×10 ml), and CH$_2$Cl$_2$ (3×10 ml). The resin B1 so far obtained, was used without any further purification.

Step (3): 1.38 ml of N,N-diisopropylethylamine (DIEA, 8.0 mmol) and acyl chloride (6.5 mmol) (C2) were added to a suspension of resin (B1) in CH$_2$Cl$_2$ (10 ml). The mixture was stirred at room temperature for 18 h, then the resin was filtered and washed with CH$_2$Cl$_2$ (3×10 ml), CH$_2$Cl$_2$/DMF in a 1/1 volume ratio (3×10 ml), DMF (3×10 ml), DMF/H$_2$O in a 9/1 volume ratio (3×10 ml), DMF (3×10 ml), DMF/MeOH in a 1/1 volume ratio (3×10 ml), MeOH (3×10 ml), CH$_2$Cl$_2$/MeOH in a 1/1 volume ratio (3×10 ml), CH$_2$Cl$_2$ (3×10 ml). The resin (C1) so far obtained, was used without any further purification.

Step (4): The resin (C1) was added to a solution of triethylsilane (0.15 ml) in TFA/DCM in a 1/1 volume ratio (15 ml) and stirred at room temperature for 15 minute. The resin was filtered and washed with solution of triethylsilane (0.15 ml) in TFA/DCM in a 1/1 volume ratio (5 ml). The solution was evaporated under vacuum to give the crude product that was purified with preparative HPLC to give compound (I) in which X, Y, Z, W, R2 and R$^1$ have the meanings given above.

g) Example of reduction of double bond in position 2-3:

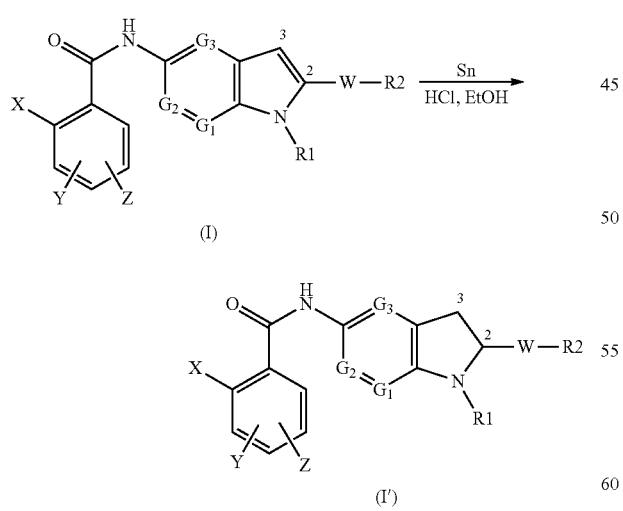

A 5-amino(aza)indole derivative (1 mmol) was dissolved in a solution of EtOH (3 ml) and HCl conc. (1.5 ml). Then, tin (5 mmol) was added and the mixture was refluxed for 6 hours. The mixture was filtered, the solution poured in a 20% KOH solution (5 ml), and extracted with Et$_2$O (3×10 ml). Organic phase was filtered on Celite and dried over Na$_2$SO$_4$. The solution was evaporated under reduced pressure. The crude product obtained was purified to give compound of formula (I') in which X, Y, Z, G1, G2, G3, R1, W and R2 have the meanings given above.

h) Example of preparation of acid from the corresponding ester:

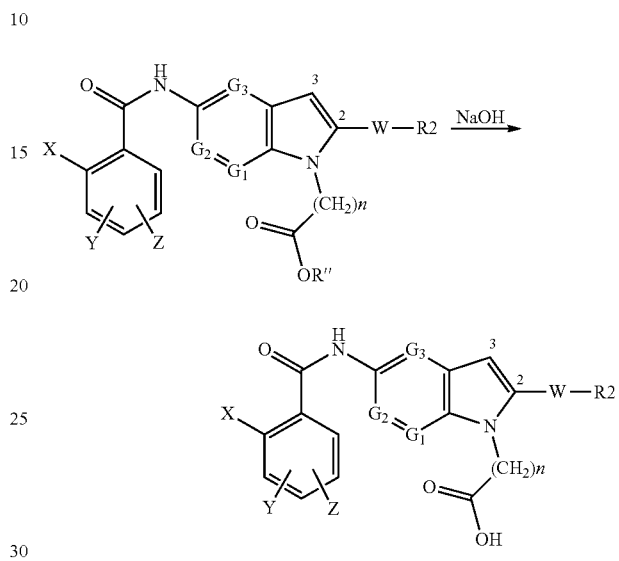

An (aza)indolester derivative (0.32 mmol) was dissolved in a solution of THF/EtOH in a 1/1 volume ratio (3 ml), then a solution of NaOH 1N was added (1.2 ml) and the mixture was stirred a room temperature for 3 h.

The organic solvents were removed under vacuum and 1N HCl solution was added until precipitation of acid. The product was filtered, washed with water and dried under vacuum to give compound of formula (I) in which X, Y, Z, G1, G2, G3, n, W and R2 have the meanings given above.

i) Example of a sixth variant of the preparation process:

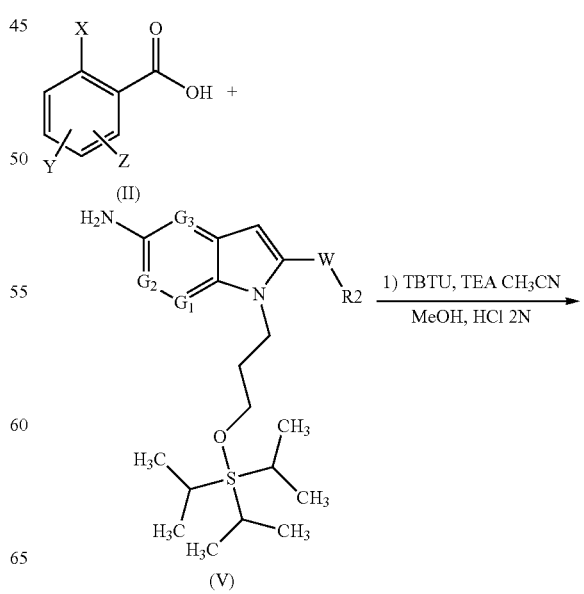

-continued

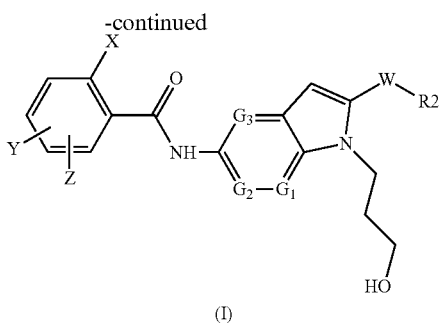

(I)

In inert atmosphere, a benzoic acid (II) (0.74 mmol), TBTU (0.86 mmol) and triethylamine (0.98 mmol) have been dissolved in anhydrous acetonitrile (3 ml). After having left the mixture under stirring at room temperature for 30 minutes, a solution of the compound (V) (0.61 mmol) in anhydrous acetonitrile (3 ml) has been added. The mixture has been left under stirring at room temperature for 3 hours, then diluted with $H_2O$ and extracted with ethyl acetate (EtOAc). After evaporation of the solvent under reduced pressure, the resulting solid (0.16 mmol) has been dissolved in MeOH (15 ml). To the solution. HCl 2N (2.5 ml) has been added, and the mixture has been left at room temperature for 3 hours. The solvent has been then evaporated under reduced pressure, and the residue dissolved in DCM and washed with a saturated solution of $NaHCO_3$. After evaporation of the organic solvent, the residue has been purified to give the compound (I) where Y, Z, G1, G2, and G3 have the meanings indicated above, W is an amidic bond, and R2 is a phenyl group.

The compounds of the present invention shown in Table 1 below were thus prepared. In Table 1 the following abbreviations with the following meanings are used:
Purification A=Crystallization
Purification B=Flash chromatography on silica gel
Purification C=Preparative HPLC (X Bridge prep. C18; 5 μm, 30×150 mm)
EtOAc=Ethyl acetate
Hex=Hexane
MeOH=Methanol
EtOH=Ethanol
$CH_3CN$=Acetonitrile
$H_2O$=Water
HCOOH=Formic acid
iPrOH=Isopropanol
$Pr_2O$=Propyl ether

TABLE 1

| Compound | Structural Formula | Example | Purification | Monoisotopic Mass | LC/MS (M + H)+ | 1H NMR (300 MHz) |
|---|---|---|---|---|---|---|
| 1 | | 2(a) | B (Hex/EtOAc; hex 90→40%) | 389.13 | 390.3 | 1H-NMR (CDCl3): 8.41 (d, J = 2.4 Hz, 1H); 8.32 (d, J = 2.4 Hz, 1H); 8.19 (s, 1H); 7.74 (m, 1H); 7.50-7.20 (om, 7H); 6.42 (s, 1H); 4.34 (q, J = 7.2 Hz, 2H); 2.42 (s, 3H); 1.27 (t, J = 7.2 Hz, 3H). |
| 2 | | 2(a) | B (Hex/EtOAc = 8/2) | 403.15 | 404.4 | 1H-NMR (CDCl3): 8.405 (d, J = 2.4 Hz, 1H); 8.30 (d, J = 2.4 Hz, 1H); 8.00 (s, 1H); 7.83 (m, 1H); 7.50-7.20 (om, 7H); 6.37 (s, 1H); 4.67 (ept. J = 6.9 Hz, 1H); 2.43 (s, 3H); 1.69 (d, J = 6.9 Hz, 6H). |
| 3 | | 2(a) | B (Hex/EtOAc = 6/4) | 419.14 | 420.4 | 1H-NMR (CDCl3): 8.45 (d, J = 2.1 Hz, 1H); 8.34 (d, J = 2.1 Hz, 1H); 8.13 (bs, 1H); 7.79 (m, 1H); 7.55-7.20 (om, 7H); 6.46 (s, 1H); 4.49 (t, J = 6.0 Hz, 2H); 3.68 (t, J = 6.0 Hz, 2H); 3.17 (s, 3H); 2.42 (s, 3H). |
| 4 | | 2(a) | B (Hex/EtOAc = 6/4) | 393.10 | 394.3 | 1H-NMR (CDCl3): 8.47 (d, J = 2.4 Hz, 1H); 8.33 (d, J = 2.4 Hz, 1H); 8.07 (s, 1H); 7.78 (m, 1H); 7.60-7.10 (2 m, 7H); 6.45 (s, 1H); 4.34 (q, J = 6.9 Hz, 2H); 1.28 (t, J = 6.9 Hz 3H) |
| 5 | | 2(a) | B (Hex/EtOAc; hex 70→60%) | 423.11 | 424.2 | 1H-NMR (CDCl3): 8.44 (d, J = 2.1 Hz); 8.33 (d, J = 2.1 Hz); 8.10 (bs, 1H); 7.78 (m, 1H), 7.65-7.10 (3 m, 7H); 6.46 (s, 1H); ); 4.44 (t, J = 5.7 Hz, 2H); 3.72 (t, J = 5.7 Hz, 2H); ); 3.18 (s, 3H); |

TABLE 1-continued

| Compound | Structural Formula | Example | Purification | Monoisotopic Mass | LC/MS (M + H)+ | 1H NMR (300 MHz) |
|---|---|---|---|---|---|---|
| 6 | [2-(4-fluorophenyl)-1-(2-methoxyethyl)-1H-indol-5-yl]-2-chlorobenzamide | 2(a) | B (Hex/EtOAc = 6/4) | 422.12 | 423.3 | 1H NMR (300 MHz, DMSO-d6) 3.07 (s, 3H) 3.54 (t, J = 5.61 Hz, 2H) 4.31 (t, J = 5.45 Hz, 2H) 6.52 (s, 1H) 7.29-7.69 (m, 10H) 8.03 (d, J = 1.65 Hz, 1H) 10.32 (s, 1H) |
| 7 | ethyl 4-[5-(2-chlorobenzamido)-2-phenyl-1H-indol-1-yl]butanoate | 2(a) | B (Hex/EtOAc 100→70%) | 460.13 | 461.7 | 1H NMR (300 MHz, DMSO-d6) 1.10 (t, J = 7.27 Hz, 3H) 1.80 (quin, J = 7.27 Hz, 2H) 2.09 (t, J = 7.10 Hz, 2H) 3.93 (q, J = 7.27 Hz, 2H) 4.25 (t, J = 7.10 Hz, 2H) 6.54 (s, 1H) 7.38-7.65 (m, 11H) 8.06 (d, J = 1.98 Hz, 1H) 10.33 (s, 1H) |
| 8 | ethyl 3-[5-(2-chlorobenzamido)-2-phenyl-1H-indol-1-yl]propanoate | 2(a) | B (Hex/EtOAc; hex 100→60%) | 446.14 | 447.7 | 1H NMR (300 MHz, DMSO-d6) 1.05 (t, J = 7.27 Hz, 3H) 2.59 (t, J = 7.27 Hz, 2H) 3.90 (q, J = 7.27 Hz, 2H) 4.48 (t, J = 7.27 Hz, 2H) 6.54 (s, 1H) 7.38-7.66 (m, 11H) 8.04 (d, J = 1.98 Hz, 1H) 10.33 (s, 1H) |

TABLE 1-continued

| Compound | Structural Formula | Example | Purification | Monoisotopic Mass | LC/MS (M + H)+ | 1H NMR (300 MHz) |
|---|---|---|---|---|---|---|
| 9 | | 2(a) | A (Hex/EtOAc = 8/2) | 417.16 | 418.7 | 1H NMR (300 MHz, DMSO-d6) 2.00 (s, 6H) 2.41 (t, J = 7.10 Hz, 2H) 4.26 (t, J = 7.10 Hz, 2H) 6.52 (s, 1H) 7.38-7.63 (m, 11H) 8.04 (d, J = 1.65 Hz, 1H) 10.32 (s, 1H) |
| 10 | | 2(a) | A (Hex/EtOAc = 8/2) | 380.17 | 381.6 | 1H NMR (300 MHz, DMSO-d6) 1.17-1.57 (m, 6H) 1.25 (t, J = 7.10 Hz, 3H) 1.61-1.87 (m, 2H) 1.88-2.06 (m, 2H) 2.61-2.83 (m, 1H) 4.16 (q, J = 6.94 Hz, 2H) 6.17 (s, 1H) 7.26-7.38 (m, 2H) 7.39-7.62 (m, 4H) 7.88 (s, 1H) 10.21 (s, 1H) |
| 11 | | 2(a) | B (Hex/EtOAc; hex 100→70%) | 432.12 | 433.8 | 1H NMR (300 MHz, DMSO-d6) 1.13 (t, J = 7.10 Hz, 3H) 4.09 (q, J = 6.94 Hz, 2H) 5.00 (s, 2H) 6.61 (s, 1H) 7.35-7.64 (m, 11H) 8.06 (s, 1H) 10.35 (s, 1H) |

TABLE 1-continued

| Compound | Structural Formula | Example | Purification | Monoisotopic Mass | LC/MS (M + H)+ | 1H NMR (300 MHz) |
|---|---|---|---|---|---|---|
| 12 | (2-chlorobenzamide indole with N-CH2CH2OCH3, phenyl at 2-position) | 2(a) | B (Hex/EtOAc = 9/1) | 404.13 | 405.6 | 1H NMR (300 MHz, DMSO-d6) 3.06 (s, 3H) 3.54 (t, J = 5.61 Hz, 2H) 4.34 (t, J = 5.78 Hz, 2H) 6.53 (s, 1H) 7.35-7.68 (m, 11H) 8.03 (d, J = 1.98 Hz, 1H) 10.32 (s, 1H) |
| 13 | (2-chlorobenzamide indole with N-(CH2)3-OAc, phenyl at 2-position) | 2(a) | A (Hex/EtOAc = 8/2) | 446.14 | 447.2 | 1H NMR (300 MHz, DMSO-d6) 1.76-1.93 (m, 2H) 1.80 (s, 3H) 3.72 (t, J = 5.94 Hz, 2H) 4.32 (t, J = 6.94 Hz, 2H) 6.54 (s, 1H) 7.38-7.64 (m, 11H) 8.05 (d, J = 1.65 Hz, 1H) 10.33 (s, 1H) |
| 14 | (2-chlorobenzamide indole with N-CH2CH2-OAc, phenyl at 2-position) | 2(a) | A (Hex/EtOAc = 8/2) | 432.12 | 433.4 | 1H NMR (300 MHz, DMSO-d6) 1.73 (s, 3H) 4.15 (t, J = 5.28 Hz, 2H) 4.47 (t, J = 5.28 Hz, 2H) 6.54 (s, 1H) 7.37-7.66 (m, 11H) 8.05 (d, J = 1.65 Hz, 1H) 10.34 (s, 1H) |

TABLE 1-continued

| Compound | Structural Formula | Example | Purification | Monoisotopic Mass | LC/MS (M + H)+ | 1H NMR (300 MHz) |
|---|---|---|---|---|---|---|
| 15 | | 2(a) | B (Hex/EtOAc 7/3) | 416.13 | 417.3 | 1H NMR (300 MHz, DMSO-d6) 1.99 (s, 3H) 2.82 (t, J = 7.43 Hz, 2H) 4.37 (t, J = 7.43 Hz, 2H) 6.54 (s, 1H) 7.24-7.74 (m, 11H) 8.05 (d, J = 1.32 Hz, 1H) 10.33 (s, 1H) |
| 16 | | 2(f) | C (CH3CN/H2O + 0.1% HCOOH 30→65%, 15 minutes) | 438.08 | 439.5 | 1H NMR (300 MHz, DMSO-d6) 2.37 (s, 3H) 3.01 (s, 3H) 6.87 (s, 1H) 7.24 (d, J = 7.60 Hz, 2H) 7.39-7.65 (m, 7H) 7.92 (d, J = 8.92 Hz, 1H) 8.18 (d, J = 1.65 Hz, 1H) 10.60 (s, 1H) |
| 17 | | 2(f) | C (CH3CN/H2O + 0.1% HCOOH 30→65%, 15 minutes) | 424.06 | 425.2 | 1H NMR (300 MHz, DMSO-d6) 3.04 (s, 3H) 6.92 (s, 1H) 7.39-7.64 (m, 10H) 7.92 (d, J = 9.08 Hz, 1H) 8.19 (d, J = 1.98 Hz, 1H) 10.60 (s, 1H) |
| 18 | | 2(f) | C (CH3CN/H2O + 0.1% HCOOH 30→65%, 15 minutes) | 430.11 | 431.4 | 1H NMR (300 MHz, DMSO-d6) 1.16-1.51 (m, 5H) 1.60-1.90 (m, 3H) 2.10 (s, 1H) 2.76 Hz, 1H) 3.04-3.19 (m, 1H) 3.21 (s, 3H) 6.66 (s, 1H) 7.42-7.61 (m, 5H) 7.83 (d, J = 9.25 Hz, 1H) 8.04 (d, J = 1.98 Hz, 1H) 10.51 (s, 1H) |

TABLE 1-continued

| Compound | Structural Formula | Example | Purification | Monoisotopic Mass | LC/MS (M + H)+ | 1H NMR (300 MHz) |
|---|---|---|---|---|---|---|
| 19 | | 2(f) | C (CH3CN/H2O + 0.1% HCOOH 30→65%, 15 minutes) | 425.06 | 426.4 | 1H NMR (300 MHz, DMSO-d6) 3.79 (s, 3H) 7.10 (s, 1H) 7.35-7.66 (m, 6H) 7.76 (d, J = 7.76 Hz, 1H) 7.86-8.04 (m, 2H) 8.22 (d, J = 1.82 Hz, 1H) 8.69 (ddd, J = 4.87, 1.73, 0.83 Hz, 1H) 10.59 (s, 1H) |
| 20 | | 2(f) | C (CH3CN/H2O + 0.1% HCOOH 30→65%, 15 minutes) | 449.06 | 450.3 | 1H NMR (300 MHz, DMSO-d6) 3.08 (s, 3H) 7.10 (s, 1H) 7.36-7.69 (m, 5H) 7.74-7.82 (m, 2H) 7.86-7.97 (m, 3H) 8.23 (d, J = 1.98 Hz, 1H) 10.64 (s, 1H) |
| 21 | | 2(f) | C (CH3CN/H2O + 0.1% HCOOH 30→65%, 15 minutes) | 452.10 | 453.4 | 1H NMR (300 MHz, DMSO-d6) 2.95-3.10 (m, 2H) 3.22 (t, J = 7.76 Hz, 2H) 3.27 (s, 3H) 6.69 (s, 1H) 7.16-7.26 (m, J = 8.48, 4.38, 4.22, 4.22 Hz, 1H) 7.31 (d, J = 4.46 Hz, 4H) 7.40-7.64 (m, 5H) 7.84 (d, J = 8.92 Hz, 1H) 8.05 (t, J = 1.57 Hz, 1H) 10.52 (s, 1H) |
| 22 | | 2(f) | C (CH3CN/H2O + 0.1% HCOOH 30→65%, 15 minutes) | 492.05 | 493.4 | 1H NMR (300 MHz, DMSO-d6) 3.06 (s, 3H) 7.09 (s, 1H) 7.40-7.73 (m, 6H) 7.75-7.82 (m, 1H) 7.85-8.00 (m, 3H) 8.22 (d, J = 1.65 Hz, 1H) 10.63 (s, 1H) |

TABLE 1-continued

| Compound | Structural Formula | Example | Purification | Monoisotopic Mass | LC/MS (M + H)+ | 1H NMR (300 MHz) |
|---|---|---|---|---|---|---|
| 23 | (2-chlorophenyl)-N-[2-(4-chlorophenyl)-1-(methylsulfonyl)-1H-indol-5-yl]benzamide | 2(f) | C (CH3CN/H2O + 0.1% HCOOH 30→65%, 15 minutes) | 458.03 | 459.5 | 1H NMR (300 MHz, DMSO-d6) 3.05 (s, 3H) 6.97 (s, 1H) 7.40-7.70 (m, 9H) 7.92 (d, J = 9.08 Hz, 1H) 8.20 (d, J = 1.82 Hz, 1H) 10.62 (s, 1H) |
| 24 | 4-[5-(2-chlorobenzamido)-1-(methylsulfonyl)-1H-indol-2-yl]phenylacetonitrile | 2(f) | C (CH3CN/H2O + 0.1% HCOOH 30→65%, 15 minutes) | 463.08 | 464.4 | 1H NMR (300 MHz, DMSO-d6) 3.05 (s, 3H) 4.12 (s, 2H) 6.94 (s, 1H) 7.33-7.72 (m, 9H) 7.92 (d, J = 8.92 Hz, 1H) 8.19 (d, J = 1.65 Hz, 1H) 10.61 (s, 1H) |
| 25 | 2-chloro-N-[1-(methylsulfonyl)-2-(2,4,5-trimethylphenyl)-1H-indol-5-yl]benzamide | 2(f) | C (CH3CN/H2O + 0.1% HCOOH 30→65%, 15 minutes) | 466.11 | 467.4 | 1H NMR (300 MHz, DMSO-d6) 2.12 (s, 3H) 2.22 (s, 3H) 2.24 (s, 3H) 3.04 (s, 3H) 6.73 (s, 1H) 7.04 (s, 1H) 7.17 (s, 1H) 7.42-7.65 (m, 5H) 7.91 (d, J = 9.08 Hz, 1H) 8.16 (d, J = 1.98 Hz, 1H) 10.58 (s, 1H) |
| 26 | 2-chloro-N-[2-(4-methoxy-2-methylphenyl)-1-(methylsulfonyl)-1H-indol-5-yl]benzamide | 2(f) | C (CH3CN/H2O + 0.1% HCOOH 30→65%, 15 minutes) | 468.09 | 469.4 | 1H NMR (300 MHz, DMSO-d6) 2.18 (s, 3H) 3.04 (s, 3H) 3.80 (s, 3H) 6.75 (s, 1H) 6.81 (dd, J = 8.26, 2.48 Hz, 1H) 6.87 (d, J = 2.64 Hz, 1H) 7.32 (d, J = 8.42 Hz, 1H) 7.41-7.66 (m, 5H) 7.91 (d, J = 8.92 Hz, 1H) 8.16 (d, J = 1.82 Hz, 1H) 10.58 (s, 1H) |

TABLE 1-continued

| Compound | Structural Formula | Example | Purification | Monoisotopic Mass | LC/MS (M + H)+ | 1H NMR (300 MHz) |
|---|---|---|---|---|---|---|
| 27 | (2-chlorobenzamide linked to 1-ethyl-2-(3-methylphenyl)indoline) | 2(g) | B (Hex/EtOAc = 8/2) | 390.15 | 391.6 | 1H NMR (300 MHz, DMSO-d6) 0.93 (t, J = 7.10 Hz, 3H) 2.32 (s, 3H) 2.69-2.89 (m, 2H) 3.13-3.40 (m, 2H) 4.61 (dd, J = 10.24, 9.25 Hz, 1H) 6.48 (d, J = 8.26 Hz, 1H) 7.05-7.61 (m, 10H) 10.11 (s, 1H) |
| 28 | (2-chlorobenzamide linked to 2-phenylindole with N-butanoic acid) | 2(h) | A (EtOH/H2O = 2:8) | 432.12 | 433.5 | 1H NMR (300 MHz, DMSO-d6) 1.79 (qd, J = 7.20, 7.06 Hz, 2H) 2.04 (t, J = 7.20 Hz, 2H) 4.22 (t, J = 7.27 Hz, 2H) 6.54 (s, 1H) 7.34-7.69 (m, 11H) 8.06 (d, J = 1.61 Hz, 1H) 10.33 (s, 1H) 12.28 (br.s, 1H) |
| 29 | (2-chlorobenzamide linked to 2-phenylindole with N-propanoic acid) | 2(h) | A (EtOH/H2O = 2:8) | 418.11 | 419.8 | 1H NMR (300 MHz, DMSO-d6) 2.54 (t, J = 7.90 Hz, 2H) 4.42 (t, J = 7.90 Hz, 2H) 6.54 (s, 1H) 7.37-7.64 (m, 11H) 8.04 (d, J = 1.83 Hz, 1H) 10.33 (s, 1H) 12.31 (br.s., 1H) |

TABLE 1-continued

| Compound | Structural Formula | Example | Purification | Monoisotopic Mass | LC/MS (M + H)+ | 1H NMR (300 MHz) |
|---|---|---|---|---|---|---|
| 30 | (2-chlorobenzamide-indole-N-CH2-COOH, 2-phenyl) | 2(h) | A (EtOH/H2O = 2:8) | 404.09 | 405.6 | 1H NMR (300 MHz, DMSO-$d_6$) 4.89 (s, 2H) 6.60 (s, 1H) 7.34-7.65 (m, 11H) 8.05 (s, 1H) 10.34 (s, 1H) 13.00 (br.s., 1H) |
| 31 | (2-chlorobenzamide-indole-N-CH2CH2-C(O)NH2, 2-phenyl) | 2(a) | A (EtOAc/EtOH= 5:1) | 417.12 | 418.2 | 1H NMR (300 MHz, DMSO-$d_6$) 2.35-2.46 (m, 2H) 4.31-4.44 (m, 2H) 6.54 (s, 1H) 6.84 (br.s., 1H) 7.33 (br.s., 1H) 7.37-7.68 (m, 11H) 8.04 (d, J = 1.98 Hz, 1H) 10.32 (s, 1H) |
| 32 | (2-chlorobenzamide-indole-N-CH2CH2-C(O)N(CH3)2, 2-phenyl) | 2(a) | A (EtOAc) | 445.16 | 446.3 | 1H NMR (300 MHz, DMSO-$d_6$) 2.63 (t, J = 7.60 Hz, 2H) 2.72 (s, 3H); 2.73 (s, 3H); 4.40 (t, J = 7.89 Hz, 2H); 6.54 (s, 1H); 7.35-7.66 (m, 11H); 8.05 (d, J = 1.75 Hz, 1H); 10.33 (s, 1H). |

TABLE 1-continued

| Compound | Structural Formula | Example | Purification | Monoisotopic Mass | LC/MS (M + H)+ | 1H NMR (300 MHz) |
|---|---|---|---|---|---|---|
| 33 | (2-chlorobenzamide, 2-phenethyl-1-ethyl-indole) | 2(a) | A (Es/AcOEt) | 402.92 | 403.3 | 1H NMR (300 MHz, DMSO-d6) δ 10.22 (s, 1H), 7.90 (s, 1H), 7.53-7.61 (m, 2H), 7.40-7.53 (m, 2H), 7.26-7.39 (m, 6H), 7.15-7.26 (m, 1H), 6.26 (s, 1H), 4.14 (q, J = 7.02 Hz, 2H), 3.04 (s, 4H), 1.22 (t, J = 7.02 Hz, 3H). |
| 34 | (2-chlorobenzamide, 2-benzyl-1-ethyl-indole) | 2(i) | A (iPrOH/AcOEt/iPr2O) | 388.89 | 389.0 | 1H-NMR (DMSO-d6): 10.23 (s, 1H); 7.89 (s, 1H); 7.49 (m, 4H); 7.26 (m, 7H); 6.17 (s, 1H); 4.15 (s, 2H); 4.09 (q, J = 6.9 Hz, 2H); 1.04 (t, J = 7.1 Hz, 3H). |
| 35 | (2-trifluoromethylbenzamide, indole-2-carboxamide with hydroxypropyl) | 2(i) | B (Es/AcOEt; Es 90→66%) | 482.45 | 482.3 | 1H-NMR (DMSO-d6): 10.41 (bs, 1H); 10.21 (bs, 1H); 8.09 (s, 1H); 7.85 (d, J = 8.5 Hz, 1H); 7.82 (m, 3H); 7.71 (m, 2H); 7.59 (d, J = 8.5 Hz, 1H); 7.49 (d, J = 8.5 Hz, 2H); 7.25 (t, J = 8.5 Hz, 2H); 7.31 (s, 1H); 7.11 (t, J = 8.5 Hz, 1H); 4.61 (t, J = 7.5 Hz, 2H); 4.47 (t, J = 5.0 Hz, 1H); 3.41 (d, J = 7.5 Hz, 2H); 1.91 (m, 2H). |
| 36 | (2,6-dichlorobenzamide, 2-(4-fluorophenyl)-1-(2-hydroxyethyl)-indole) | 2(a) | B (Es/AcOEt; Es 90→60%) | 443.30 | 443.2 | 1H NMR (300 MHz, DMSO-d6) δ 10.53 (s, 1H), 8.00 (d, J = 1.98 Hz, 1H), 7.63-7.73 (m, 2H), 7.45-7.61 (m, 4H), 7.27-7.41 (m, 3H), 6.53 (s, 1H), 4.89 (t, J = 5.28 Hz, 1H), 4.20 (t, J = 6.28 Hz, 2H), 3.63 (q, J = 6.17 Hz, 2H). |

TABLE 1-continued

| Compound | Structural Formula | Example | Purification | Monoisotopic Mass | LC/MS (M + H)+ | 1H NMR (300 MHz) |
|---|---|---|---|---|---|---|
| 37 | (4-F, 2-CF3-benzamide linked to 2-(4-chlorophenyl)-1-(2-hydroxyethyl)indol-5-yl) | 2(a) | B (Es/AcOEt; Es 90→60%) | 476.85 | 477.2 | 1H NMR (300 MHz, DMSO-d6) δ 10.39 (s, 1H), 7.98 (d, J = 1.98 Hz, 1H), 7.73-7.84 (m, 2H), 7.54-7.71 (m, 5H), 7.51 (d, J = 8.92 Hz, 1H), 7.36 (dd, J = 2.15, 8.75 Hz, 1H), 6.56 (s, 1H), 4.88 (t, J = 6.11 Hz, 1H), 4.21 (t, J = 6.11 Hz, 2H), 3.63 (q, J = 6.06 Hz, 2H) |
| 38 | (2-F, 6-CF3-benzamide linked to 2-(4-fluorophenyl)-1-(2-hydroxyethyl)indol-5-yl) | 2(a) | B (Es/AcOEt; Es 90→60%) | 460.40 | 461.4 | 1H NMR (300 MHz, DMSO-d6) δ 10.60 (s, 1H), 7.97 (d, J = 1.98 Hz, 1H), 7.60-7.81 (m, 5H), 7.51 (d, J = 8.92 Hz, 1H), 7.26-7.41 (m, 3H), 6.53 (s, 1H), 4.89 (t, J = 5.45 Hz, 1H), 4.20 (t, J = 6.11 Hz, 2H), 3.63 (q, J = 6.17 Hz, 2H) |

EXAMPLE 3

In Vitro Biological Activity

The test used makes it possible to evaluate the inhibitory capacity of the test compounds on the production of $PGE_2$ and the selectivity relative to the production of $PGF_{2\alpha}$. The human pulmonary adenocarcinoma cell line A549 was used, which is particularly sensitive to stimulation with proinflammatory cytokines, for instance $IL-1_\beta$, and, in response to this stimulation, is particularly active in the production and release of two prostanoids: $PGE_2$ and $PGF_{2\alpha}$ (Thoren S. Jakobsson P-J, 2000).

The cells were stimulated with $IL-1_\beta$ (10 ng/ml) and simultaneously treated with the test compound for 22 hours in a suitable culture medium (DMEM Dulbecco's Modified Eagles Medium) enriched with 5% fetal calf serum and L-glutamine (4 mM final) in an incubator at 37° C. and with a $CO_2$ concentration of 5%.

At the end of the incubation, the amount of $PGE_2$ and $PGF_{2\alpha}$ produced and released into the supernatant were assayed using an EIA kit (produced and sold by Cayman Chemicals, Ann Arbor, Mich., USA).

The comparative compound used was indomethacin at a concentration of 10 nM (Sigma-Aldrich), which is a non-steroidal anti-inflammatory drug that inhibits in equal measure both $PGE_2$ and $PGF_{2\alpha}$.

The results, expressed as a percentage of inhibition of the production of $PGE_2$ and of $PGF_{2\alpha}$ at a concentration of 10 μM, are given in Table 2, in which "ia" (inactive) indicates an inhibitory activity of less than 20%.

TABLE 2

| | % inhibition at 10 μM | |
|---|---|---|
| Compound | $PGE_2$ | $PGF_{2\alpha}$ |
| 1 | 59 | ia |
| 7 | 76 | ia |
| 10 | 78 | ia |
| 12 | 78 | ia |
| 13 | 61 | ia |
| 21 | 69 | ia |
| 22 | 94 | 44 |
| 33 | 41 | ia |
| 34 | 83 | 44 |
| 35 | 88 | 13 |
| 36 | 40 | ia |
| 37 | 73 | ia |
| 38 | 42 | ia |
| Indomethacin (10 nM) | 100 | 100 |

For illustrative purposes, Table 3 collates the $pIC_{50}$ values of a number of compounds of the invention, where $pIC_{50}$ represents the negative logarithm of the $IC_{50}$, which, in turn, represents the concentration of compound that inhibits the production of $PGE_2$ or $PGF_{2\alpha}$ by 50% relative to cells that are stimulated but not treated with the same compound.

In Table 3, "nd" means not determinable.

TABLE 3

| | $pIC_{50}$ | |
|---|---|---|
| Compound | $PGE_2$ | $PGF_{2\alpha}$ |
| 7 | 5.4 | nd |
| 10 | 5.8 | nd |
| 12 | 5.5 | nd |
| 13 | 5.1 | nd |

TABLE 3-continued

| | $pIC_{50}$ | |
|---|---|---|
| Compound | $PGE_2$ | $PGF_{2\alpha}$ |
| 21 | 6.3 | nd |
| 22 | 5.8 | 4.6 |
| 34 | 5.6 | nd |
| 35 | 5.6 | 4.5 |
| 36 | 4.3 | nd |
| 37 | 5.2 | nd |
| 38 | 4.6 | nd |
| Indomethacin | 8.3 | 8.6 |

EXAMPLE 4

In Vivo Biological Activity

The test compound was evaluated in the model of acetic acid-induced stretching in mice (Stock J. L. et al., J Clin Inv 2001, 107: 325-331). This test makes it possible to evaluate the antinociceptive activity of the compounds of the invention in a model of inflammatory pain.

Female CD-1 mice weighing 25-30 g were used for the test. The animals were treated intraperitoneally with the test compound (0.1-10 mg/kg) suspended in methylcellulose (MTC). The control animals were treated with the vehicle alone (MTC) via the same route.

30 minutes after the treatment, the animals received an intraperitoneal injection of acetic acid (0.7 v/v in physiological solution, 16 μl/g of body weight) in order to induce inflammatory pain and to check the effects of the test compound on the nociceptive response.

Immediately after the administration of acetic acid and for the following 20 minutes, the number of stretches, which represents the parameter for evaluation of the nociceptive response, was measured.

As reported in Table 4, the compound of the invention induced, in a dose-dependent manner, a reduction in stretching in the 20 minutes following the administration of acetic acid, compared with the animals treated with MTC alone.

TABLE 4

| Treatment | dose (mg/kg) | N° of stretches | % inhibition |
|---|---|---|---|
| Vehicle | — | 50 ± 3.3 | |
| Compound 10 | 0.01 | 47 ± 4.3 | 5.9 ± 8.76 |
| | 0.1 | 34 ± 3.2 | 33.2 ± 6.16 |
| | 1 | 33 ± 3.9 | 33.6 ± 8.04 |
| | 10 | 21 ± 3.2 | 57.5 ± 6.57 |

EXAMPLE 5

Selectivity between Isoforms of PGES

The test used makes it possible to evaluate the capacity of the compounds of the invention to inhibit the production of $PGE_2$ in a human lymphoma cell line U-937 that preferentially expresses an enzymatic isoform (cPGES), which is responsible for the production of $PGE_2$ under basal conditions, in the absence of pro-inflammatory stimuli. This enzymatic form is different from the one predominantly expressed in the A549 cells (mPGES-1) after a pro-inflammatory stimulus.

The absence of inhibitory activity on $PGE_2$ in this cell model ensures the selectivity of the compound compared with the enzymatic form responsible for the production of PGE₂ in the presence of inflammatory stimuli.

The results, expressed as a percentage of inhibition of the production of PGE₂, are given in Table 5, in which "ia" (inactive) indicates an inhibitory activity of less than 20%. The reference compound used was indomethacin at a concentration of 10 nM.

The compounds of the invention were found not to significantly inhibit the production of PGE₂ owing mainly to the action of cPGES.

TABLE 5

| Compound | % inhibition at 10 μM PGE₂ |
|---|---|
| 10 | ia |
| 12 | ia |
| 13 | ia |
| 22 | ia |
| Indomethacin (10 nM) | 100 |

The invention claimed is:

1. An intermediate compound represented by formula (III)

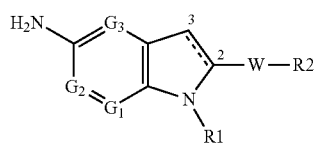

(III)

wherein
G1, G2, and G3 are a CH group;
R1 is a $(C_1-C_6)$alkyl, $(C_3-C_7)$cycloalkyl, $(C_1-C_6)$alkylOR$^I$, $(CH_2)_n$CONR$^{II}$R$^{III}$, $(CH_2)_n$COR$^I$, $(CH_2)_n$COOR$^{II}$, $(CH_2)_n$OCOR$^I$, SO$_2$R$^I$, $(CH_2)_n$NR$^{II}$SO$_2$R$^I$, or $(CH_2)_n$SO$_2$R$^I$ group, optionally substituted with 1 to 3 hydroxy groups, wherein n is an integer from 1 to 6, R$^I$ is a $(C_1-C_3)$alkyl, or $(C_1-C_3)$alkylOH group, and R$^{II}$ and R$^{III}$, which may be identical or different, are a hydrogen atom or a $(C_1-C_3)$alkyl group;
W is a σ bond, or a $(C_1-C_6)$alkyl, $(C_2-C_6)$alkenyl, O$(C_1-C_6)$alkyl, O$(C_2-C_6)$alkenyl, C(O)NH, $(CH_2)_p$CO$(CH_2)_q$, or $(CH_2)_p$C(OH)$(CH_2)_q$ group, wherein p and q, which may be identical or different, are an integer from 0 to 3;
R2 is a phenyl, pyridyl, or $(C_4-C_7)$cycloalkyl group, optionally substituted with 1 to 3 substituents, which may be identical or different, represented by L-M, wherein L is a σ bond, or a $(C_1-C_6)$alkyl, $(C_2-C_6)$alkenyl, $(C_2-C_6)$alkinyl, O$(C_1-C_6)$alkyl, O$(C_2-C_3)$alkenyl, or O$(C_2-C_6)$alkinyl group, and M is a hydrogen or halogen atom, or a OH, CF₃, NO₂, CN, COOR$^{II}$, SO₂NHR$^{II}$, CH₂CONR$^{II}$R$^{III}$, NR$^{II}$R$^{III}$, SO₂R$^{IV}$, NHSO₂R$^{IV}$, POR$^{IV}$R$^V$, or OPOR$^{IV}$R$^V$ group, wherein R$^{II}$ and R$^{III}$, which may be identical or different, have the meaning above, and R$^{IV}$ and R$^V$, which may be identical or different, are a $(C_1-C_3)$alkyl group; and
the dotted line between the carbon atoms at the 2 and 3 positions means that the bond can be a single bond or a double bond;
provided that
when R1 is a $(C_1-C_6)$alkyl or $(C_3-C_7)$cycloalkyl group, optionally substituted with 1 to 3 hydroxy groups, W is a σ bond, and the bond between the carbon atoms in the 2 and 3 position is a double bond, then
R2 is not a phenyl or pyridyl group, optionally substituted with 1 to 3 substituents, which may be identical or different, selected from the group consisting of a halogen, $(C_1-C_6)$alkyl optionally substituted with a hydroxy group, trifluoromethyl, nitro, amino, di$(C_1-C_3)$alkylamino, hydroxy, $(C_1-C_3)$alkoxy, COOH, COOR$^{II}$, SO₂CH₃, SO₂NHCH₃, NHSO₂CH₃, POR$^{IV}$R$^V$, OPOR$^{IV}$R$^V$, $(C_1-C_6)$alkyl-COOH, and $(C_2-C_6)$alkenyl-COOH.

2. An intermediate compound according to claim 1, wherein R1 is:
a $(C_1-C_3)$alkyl, $(C_1-C_3)$alkylOR$^I$, $(CH_2)_n$NR$^{II}$R$^{III}$, $(CH_2)_n$CONR$^{II}$R$^{III}$, $(CH_2)_n$COR$^I$, $(CH_2)_n$COOR$^{II}$, $(CH_2)_n$OCOR$^I$, SO$_2$R$^I$, $(CH_2)_n$NR$^{II}$SO$_2$R$^I$, or $(CH_2)_n$SO$_2$R$^I$ group, optionally substituted with 1 to 3 hydroxy groups, wherein n is an integer from 1 to 4, R$^I$ is a $(C_1-C_3)$alkyl or $(C_1-C_3)$alkylOH group, and R$^{II}$ and R$^{III}$, which may be identical or different, are a hydrogen atom or a $(C_1-C_3)$alkyl group; or
a $(C_1-C_3)$alkyl, $(C_1-C_3$alkylOR$^I$, $(CH_2)_n$CONR$^{II}$R$^{III}$, $(CH_2)_n$COR$^I$, $(CH_2)_n$COOR$^{II}$, $(CH_2)_n$OCOR$^I$, SO$_2$R$^I$, $(CH_2)_n$NR$^{II}$SO$_2$R$^I$, or $(CH_2)_n$SO$_2$R$^I$ group, optionally substituted with 1 to 3 hydroxy groups, wherein n is an integer from 1 to 3, R$^I$ is a CH₃, C₂H₅, CH₂OH, a C₂H₄OH group, and R$^{II}$ and R$^{III}$, which may be identical or different, are a hydrogen atom or a CH₃, C₂H₅ group.

3. An intermediate compound according to claim 1, wherein W is:
a σ bond, a $(C_1-C_3)$alkyl, $(C_2-C_4)$alkenyl, O$(C_1-C_3)$alkyl, O$(C_2-C_3)$alkenyl, C(O)NH, $(CH_2)_p$CO$(CH_2)_q$, or $(CH_2)_p$ C(OH)$(CH_2)_q$ group, wherein p and q, which may be identical or different, are an integer from 1 to 3; or
a σ bond, a CH₂, C₂H₄, CH=CH, OCH₂, OC₂H₄, OCH=CH, C(O)NH, $(CH_2)_p$CO$(CH_2)_q$, or $(CH_2)_p$C(OH)$(CH_2)_q$ group, wherein p and q, which may be identical or different, are an integer from 1 to 2.

4. An intermediate compound according to claim 1, wherein R2 is:
a phenyl, pyridyl, or $(C_3-C_7)$cycloalkyl group, optionally substituted with 1 to 2 substituents, which may be identical or different, represented by an L-M, wherein L is a σ bond, or a $(C_1-C_3)$alkyl, $(C_2-C_4)$alkenyl, $(C_2-C_4)$alkinyl, O$(C_1-C_3)$alkyl, O$(C_2-C_4)$alkenyl, or O$(C_2-C_4)$alkinyl group, and M is a hydrogen or halogen atom, or a CF₃, CN, COOR$^{II}$, SO₂NHR$^{II}$, CH₂CONR$^{II}$R$^{III}$, NR$^{II}$R$^{III}$, SO₂R$^{IV}$, NHSO₂R$^{IV}$, POR$^{IV}$R$^V$, or OPOR$^{IV}$R$^V$ group, wherein R$^{II}$ and R$^{III}$, which may be identical or different, are a hydrogen atom or a $(C_1-C_3)$alkyl group, and R$^{IV}$ and R$^V$, which may be identical or different, are a $(C_1-C_3)$alkyl group; or
a phenyl, pyridyl, or $(C_3-C_7)$cycloalkyl group, optionally substituted with 1 substituent represented by an L-M, wherein L is a σ bond, or a CH₂, C₂H₄, CH=CH, C≡C, OCH₂, OC₂H₄, OCH=CH, OC≡C group, and M is a hydrogen or halogen atom, or a CF₃, CN, COOR$^{II}$, SO₂NHR$^{II}$, CH₂CONR$^{II}$R$^{III}$, NR$^{II}$R$^{III}$, SO₂R$^{IV}$, NHSO₂R$^{IV}$, POR$^{IV}$R$^V$, or OPOR$^{IV}$R$^V$ group, wherein R$^{II}$ and R$^{III}$, which may be identical or different, are a hydrogen atom or a CH₃, C₂H₅ group, and R$^{IV}$ and R$^V$, which may be identical or different, are a CH₃ or C₂H₅ group.

5. An intermediate compound according to claim 1, wherein W is σ bond, or a CH₂ or C₂H₄ group; and
R2 is a phenyl group optionally substituted with 1 to 3 substituents, which may be identical or different, selected from the group consisting of Br, Cl, F, $CH_3$, $C_2H_5$, $OCH_3$, $OC_2H_5$, CN, $CH_2CN$, and $CH_2CONH_2$;

a cyclohexyl group optionally substituted with 1 to 3 substituents, which may be identical or different, selected from the group consisting of Br, Cl, F, $CH_3$, $C_2H_5$, $OCH_3$, $OC_2H_5$, CN, $CH_2CN$, and $CH_2CONH_2$; or a pyridyl group optionally substituted with 1 to 3 substituents, which may be identical or different, selected from the group consisting of Br, Cl, F, $CH_3$, $C_2H_5$, $OCH_3$, $OC_2H_5$, CN, $CH_2CN$, and $CH_2CONH_2$.

* * * * *